United States Patent
Ito et al.

(10) Patent No.: US 9,493,129 B2
(45) Date of Patent: *Nov. 15, 2016

(54) DRIVE CONTROL APPARATUS AND METHOD FOR PROVIDING A DRIVE CONTROL TO A HYBRID ELECTRIC VEHICLE, AND HYBRID ELECTRIC VEHICLE

(75) Inventors: Yoshiki Ito, Shizuoka (JP); Masaaki Tagawa, Shizuoka (JP); Masakazu Saito, Shizuoka (JP); Hitoshi Ohkuma, Shizuoka (JP); Yukihiro Hosoe, Shizuoka (JP)

(73) Assignee: SUZUKI MOTOR CORPORATION, Shizuoka (JP)

( * ) Notice: Subject to any disclaimer, the term of this patent is extended or adjusted under 35 U.S.C. 154(b) by 647 days.

This patent is subject to a terminal disclaimer.

(21) Appl. No.: 13/981,586

(22) PCT Filed: Feb. 3, 2011

(86) PCT No.: PCT/JP2011/000622
§ 371 (c)(1),
(2), (4) Date: Jul. 24, 2013

(87) PCT Pub. No.: WO2012/104924
PCT Pub. Date: Aug. 9, 2012

(65) Prior Publication Data
US 2013/0307329 A1 Nov. 21, 2013

(51) Int. Cl.
*B60L 1/00* (2006.01)
*B60R 16/033* (2006.01)
(Continued)

(52) U.S. Cl.
CPC ............. *B60R 16/033* (2013.01); *A61B 6/037* (2013.01); *B60K 6/445* (2013.01); *B60W 10/06* (2013.01);
(Continued)

(58) Field of Classification Search
CPC ..... B60K 6/445; B60W 10/06; B60W 20/00; B60W 2710/0644; A61B 6/037; Y02T 10/6239; G01T 1/20; G06T 7/0012; B60R 16/033; B60Y 2300/92
USPC ....................................................... 307/10.1
See application file for complete search history.

(56) References Cited

U.S. PATENT DOCUMENTS 9,221,455 B2 * 12/2015 Ito .......................... B60K 6/445
2005/0284671 A1 12/2005 Tatara et al.
(Continued)

FOREIGN PATENT DOCUMENTS

| JP | 2004-129373 A | 4/2004 |
| JP | 2007-296937 A | 11/2007 |
| JP | 2008-12992 A | 1/2008 |
| JP | 2009-280094 A | 12/2009 |

OTHER PUBLICATIONS

The First Office Action mailed May 6, 2015 in corresponding Chinese Patent Application No. 201180066658.7 (with an English translation) (10 pages).
(Continued)

*Primary Examiner* — Jared Fureman
*Assistant Examiner* — Duc M Pham
(74) *Attorney, Agent, or Firm* — Rothwell, Figg, Ernst & Manbeck, P.C.

(57) ABSTRACT

An arrangement which prevents excessive engine speed, satisfies a driver's requested torque and protects a battery from overvoltage. A control apparatus provides a torque control to a hybrid electric vehicle, and calculates an engine speed final target so that an engine speed temporary target does not exceed an upper limit. In addition, the control recalculates an engine operating point target based on the calculated engine speed final target, and calculates an engine power final target based on the recalculated engine operating point target. An electrical power target is calculated and may not exceed an upper limit for battery charging and an upper limit for battery discharging. Engine torque is controlled based on the calculated engine operating point target (especially the engine torque final target). Motor generators are controlled to operate based on the calculated engine operating point target and electrical power target.

6 Claims, 16 Drawing Sheets

(51) Int. Cl.

| | |
|---|---|
| *B60K 6/445* | (2007.10) |
| *B60W 10/06* | (2006.01) |
| *B60W 10/26* | (2006.01) |
| *B60W 20/00* | (2016.01) |
| *G01T 1/20* | (2006.01) |
| *G06T 7/00* | (2006.01) |
| *G01T 1/164* | (2006.01) |
| *A61B 6/03* | (2006.01) |

(52) U.S. Cl.
CPC .............. *B60W 10/26* (2013.01); *B60W 20/00* (2013.01); *G01T 1/1644* (2013.01); *G01T 1/20* (2013.01); *G06T 7/0012* (2013.01); *B60W 2710/0644* (2013.01); *B60W 2710/0666* (2013.01); *B60Y 2300/92* (2013.01); *Y02T 10/6239* (2013.01)

(56) References Cited

U.S. PATENT DOCUMENTS

2013/0311024 A1\* 11/2013 Tagawa .................. B60K 6/445
701/22
2013/0311025 A1\* 11/2013 Tagawa ............... B60W 30/184
701/22
2013/0311029 A1\* 11/2013 Tagawa .................. B60K 6/445
701/22

OTHER PUBLICATIONS

International Search Report mailed Apr. 19, 2011 in PCT/JP2011/000622.
Notice of Allowance mailed Jan. 5, 2016 in corresponding Chinese Patent Application No. 201180066658.7 (2 pages).

\* cited by examiner

DRIVE CONTROL APPARATUS AND METHOD FOR PROVIDING A DRIVE CONTROL TO A HYBRID ELECTRIC VEHICLE, AND HYBRID ELECTRIC VEHICLE

CROSS REFERENCE TO RELATED APPLICATION

This application is a 35 U.S.C. 371 National Phase Entry Application from PCT/JP2011/000622, filed Feb. 3, 2011, the disclosure of which is incorporated herein in its entirety by reference.

TECHNICAL FIELD

The present invention relates to technology associated with a hybrid electric vehicle including, as power sources, an engine and motor generators.

BACKGROUND ART

In a drive control apparatus for providing a drive control to a hybrid electric vehicle by driving a drive shaft connected to traction wheel(s) by composing output of an engine and outputs of first and second motor generators, there is a technology of: calculating a charge/discharge power target based on a battery SOC (state of charge) together with calculating a drive power target requested by the vehicle driver based on a drive torque target, which has, as parameters, an accelerator pedal position and a vehicle speed, and the vehicle speed; calculating, as an engine power target, the sum of the calculated drive power target and the calculated charge/discharge power target; and calculating an engine operating point from the calculated engine power target (see Patent Literature 1, for example).

In such drive control apparatus for providing a drive control to a hybrid electric vehicle, first and second motor generators are controlled to operate in power running mode or regenerating mode together with controlling the engine torque and engine speed so that the engine may operate at the calculated engine operating point target (see Patent Literatures 1 and 2, for example).

PRIOR ART

Patent Literature

Patent Literature 1: JP-A 2008-12992
Patent Literature 2: JP-A 2007-296937

SUMMARY OF INVENTION

Problem to be Solved by Invention

In the above mentioned drive control apparatus for providing a drive control to a hybrid electric vehicle, since a balance is kept between, for example, the engine speed and the motor generator speed(s), there is need to prevent the engine speed from becoming high if the motor generator speed is to be kept lower than or equal to a desired speed.

On the other hand, in said drive control apparatus for providing a drive control to a hybrid electric vehicle, if the engine speed is prevented from becoming high, this results in preventing the engine output from becoming high, providing drive torque less than requested by the vehicle driver, making it difficult to satisfy the drive torque requested by the vehicle driver.

Moreover, in this case, the motor generators might be controlled to operate in power running mode or regenerating mode to provide drive torque as requested by the vehicle driver or the maximum possible effort to secure drive torque, even if restricted from his/her requests, in order to follow them, but, in doing so, it is necessary to prevent overvoltage during battery charge/discharge from the standpoint of battery protection.

An object of the present invention is to both prevent the engine speed from increasing too high and satisfy the drive torque requested by the vehicle driver while protecting the battery from overvoltage, overdischarge and overcharge.

Means to Solve Problem

In order to solve said problem, there is provided, according to an embodiment of the present invention, a drive control apparatus for providing a drive control to a hybrid electric vehicle by controlling an engine and motor generators, which are operable to give a charge of electrical power to a battery and receive a supply of electrical power from said battery, to power the vehicle with driving force derived from said engine and said motor generators, the drive control apparatus comprising: a drive power target calculation function for calculating a drive power target based on an accelerator pedal position and the vehicle speed; a charge/discharge target calculation function for calculating a charge/discharge electrical power target to/from said battery based on a state of charge/discharge of said battery; an engine power first target calculation function for calculating an engine power first target based on the drive power target, which is calculated by said drive power target calculation function, and the charge/discharge electrical power target, which is calculated by said charge/discharge electrical power target calculation function; an engine operating point first target calculation function for calculating an engine speed first target and an engine torque first target, both of which correspond to the engine power first target calculated by said engine power first target calculation function, based on information of the engine operating point identified by the relation between engine speed and engine torque; an engine speed first target upper limit calculation function for calculating an upper limit of said engine speed first target based on the vehicle speed; an engine speed second target calculation function for calculating an engine speed second target indicative of the engine speed first target which is calculated by said engine operating point calculation function so as not to exceed that upper limit of the engine speed first target which is calculated by said engine speed first target upper limit calculation function; an engine torque second target calculation function for calculating an engine torque second target, which corresponds to said engine speed second target calculated by said engine speed second target calculation function, based on said information of the engine operating point; an engine power second target calculation function for calculating an engine power second target based on the engine speed second target which is calculated by said engine speed second target calculation function and the engine torque second target which is calculated by said engine torque second target calculation function; an electrical power upper and lower limit calculation function for calculating an electrical power upper limit for battery charging and an electrical power upper limit for battery discharging based on the state of said battery; an electrical power target calculation function for calculating an electrical power target indicative of the amount of electrical power to be generated by driving said motor generators to charge said battery or to be provided by said battery to said motor generators to drive said motor generators, based on a difference between the drive power target which is calculated by said drive power target calculation function and the engine power second target which is calculated by said engine power second target calculation function, so that said calculated electrical power target may not exceed the electrical power upper limit for battery charging and the electrical power upper limit for battery discharging which are calculated by said electrical power upper limit calculation function; an engine control configured to control torque of said engine based on the engine torque second target which is calculated by said engine torque second target calculation function; and a motor generator control configured to control said motor generators based on the engine speed second target which is calculated by said engine speed second target calculation function, the engine torque second target which is calculated by said engine torque second target calculation function, and the electrical power target which is calculated by said electrical target calculation function.

That is, the embodiment of the present invention calculates an engine speed second target so that an engine speed first target on an engine operating point target, which is calculated from an engine power first target initially calculated, may not exceed an upper limit; recalculates an engine operating point target based on the calculated engine speed second target; calculates an engine power second target based on the recalculated engine operating point target; calculates an electrical power target based on the calculated engine power second target in order not to exceed electrical power upper limits for battery charging and battery discharging which are calculated according to the state of the battery; controls torque of the engine based on the calculated engine operating point target (especially the engine torque second target); and controls the motor generators, i.e. operating the motor generators in power running mode or regenerating mode, based on the calculated engine operating point target and electrical power target.

Moreover, it is preferable in the embodiment of the present invention that there are further provided a lookup table accessible by battery temperature for relating battery temperature to corresponding values of an electrical power upper limit for battery charging and also to corresponding values of an electrical power upper limit for battery discharging; and a lookup table accessible by battery voltage for relating battery voltage to corresponding values of an electrical power upper limit for battery charging and also to corresponding values of an electrical power upper limit for battery discharging, wherein, among the electrical power upper limits, one for battery charging and the other for battery discharging, obtained versus battery temperature by referring to the lookup table accessible by battery temperature and the electrical power upper limits, one for battery charging and the other for battery discharging, obtained versus battery voltage by referring to the lookup table accessible by battery voltage, said electrical power upper and lower limit calculation function evaluates each of the obtained upper limits according to how much the electrical power target is restricted to finally determine that one of the obtained upper limits for battery charging which has the greatest amount when the electrical power target is restricted and that one of the obtained upper limits for battery discharging which has the greatest amount when the electrical power target is restricted.

Moreover, it is preferable in the embodiment of the present invention that there is further provided a lookup table accessible by battery state of charge (SOC) for relating battery SOC to corresponding values of an electrical power upper limit for battery charging and also to corresponding values of an electrical power upper limit for battery discharging, wherein, among the electrical power upper limits, one for battery charging and the other for battery discharging, obtained versus battery temperature by referring to the lookup table accessible by battery temperature; the electrical power upper limits, one for battery charging and the other for battery discharging, obtained versus battery voltage by referring to the lookup table accessible by battery voltage; and the electrical power upper limits, one for battery charging and the other for battery discharging, obtained versus the state of charge of said battery by referring to the lookup table accessible by battery SOC, said electrical power upper and lower limit calculation function evaluates each of the obtained upper limits according to how much the electrical power target is restricted to finally determine that one of the obtained upper limits for battery charging which has the greatest amount when the electrical power target is restricted and that one of the obtained upper limits for battery discharging which has the greatest amount when the electrical power target is restricted.

Moreover, in the embodiment of the present invention, it is preferable that there is provided a power split and composition system having four axes with each of rotary elements of two planetary gear arrangements connected; that two motor generators are connected to said battery; that, in a manner that one of said motor generators, said engine, a drive shaft connected to a traction wheel, and the other of said motor generators are located on a collinear diagram, the four axes of said power split and composition system are connected to said one motor generator, said engine, said drive shaft and said the other motor generator, respectively; that an upper limit of said engine speed is restricted by an upper limit of rotational speed of said one motor generator and undergoes a change depending on the vehicle speed; and that said engine speed first target upper limit calculation function calculates the upper limit of said engine speed first target based on said vehicle speed and an upper limit of rotational speed of said one motor generator.

Moreover, according to the embodiment of the present invention, there is provided a hybrid electric vehicle with the drive control apparatus mentioned in the foregoing description.

Moreover, according to the embodiment of the present invention, there is provided a drive control method for providing a drive control to a hybrid electric vehicle by controlling an engine and motor generators, which are operable to give a charge of electrical power to a battery and receive a supply of electrical power from said battery, to power the vehicle with driving force derived from said engine and said motor generators, the drive control method comprising the steps of: calculating a drive power target based on an accelerator pedal position and the vehicle speed; calculating a charge/discharge electrical power target to/from said battery based on a state-of-charge/discharge of said battery; calculating an engine power first target based on said drive power target and said charge/discharge electrical power target; calculating an engine speed first target and an engine torque first target, both of which correspond to said engine power first target, based on information of the engine operating point identified by the relation between engine speed and engine torque; calculating an upper limit of said engine speed first target based on the vehicle speed; calculating an engine speed second target indicative of the engine speed first target so as not to exceed said upper limit of the engine speed first target; calculating an engine torque second target, which corresponds to said engine speed second target, based on said information of engine operating point; calculating an engine power second target based on said engine speed second target and said engine torque second target; calculating an electrical power upper limit for battery charging and an electrical power upper limit for battery discharging based on the state of said battery; calculating an electrical power target indicative of the amount of electrical power to be generated by driving said motor generators to charge said battery or to be provided by said battery to said motor generators to drive said motor generators, based on a difference between said drive power target and said engine power second target, so that said calculated electrical power target may not exceed the electrical power upper limit for battery charging and the electrical power upper limit for battery discharging; and controlling said motor generators based on said engine speed second target, said engine torque second target, and said electrical power target together with controlling torque of said engine based on said engine torque second target.

Effect of Invention

The embodiment of the present invention prevents the engine speed from becoming too high by calculating an engine speed target so that it may not exceed the upper limit, and enables the motor generators to operate in power running mode by calculating an electrical power target based on the engine speed target calculated not to exceed the upper limit, thus compensating for a reduction in the engine output to satisfy drive torque requested by the vehicle driver.

Moreover, according to the embodiment of the present invention, it is possible to protect the battery from overvoltage, overdischarge and overcharge in accordance with the battery state of charge by calculating the electrical power target so that it may not exceed the upper limits which are calculated in accordance with the battery state for use during charge or discharge of the battery.

DESCRIPTION OF EMBODIMENT(S)

Referring, next, to the drawings, one embodiment of a drive control apparatus for providing a drive control to a hybrid electric vehicle according to the present invention is described.

(Configuration Of Drive Control Apparatus for Hybrid Electric Vehicle)

Figure 1:
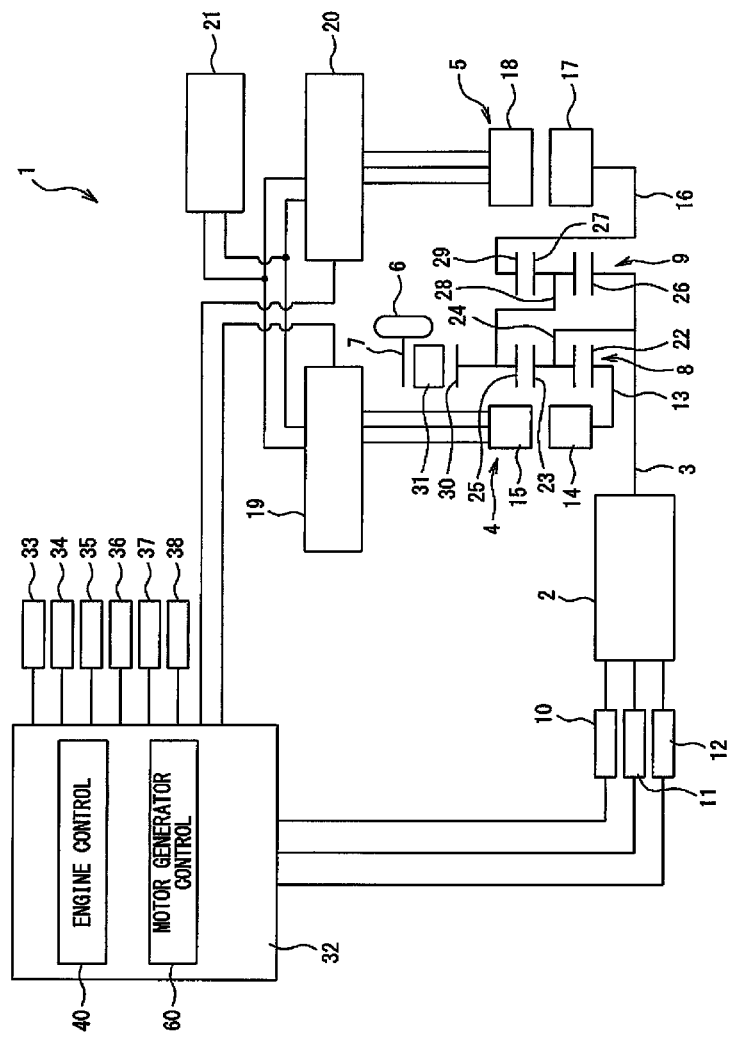
FIG. 1 shows an exemplary system configuration diagram showing one embodiment of a drive control apparatus for providing a drive control to a hybrid electric vehicle according to the present invention.

FIG. 1 shows an example of system configuration diagram showing one embodiment of a drive control apparatus 1 for providing a drive control to a hybrid electric vehicle according to the present invention (called hereinafter "a drive control apparatus".

Referring now to FIG. 1, as its powertrain, the hybrid electric vehicle includes: an engine (an internal combustion engine) 2 that may provide drive power generated due to internal combustion of fuel, a first motor generator (a dynamotor) 4 and a second motor generator (a dynamotor) 5, each of which is able to generate drive power by electrical energy (power running) or electrical energy by regeneration, a drive shaft 7 connected to traction wheels 6 of the vehicle, a first and a second planetary gear arrangements 8 and 9, which provide a power split and composition system that composes or splits drive power from engine 2, first motor generator 4 and second motor generator 5 and ground reaction that is delivered from the traction wheels 6, and an output gearing 31 that provides a drive connection between the power split and composition system and drive shaft 7.

First motor generator 4 has a first rotor shaft 13, a first rotor 14 and a first stator 15. Second motor generator 5 has a second rotor shaft 16, a second rotor 17 and a second stator 18.

First stator 15 of first motor generator 4 is electrically coupled to a first inverter 19, and second stator 18 of second motor generator 5 is electrically coupled to a second inverter 20. First and second inverters 19 and 20 are electrically coupled to a battery 21. First and second inverters 19 and 20 control the amount of electrical energy delivered from the battery 21 to first and second stators 15 and 18. First and second inverters 19 and 20 are electrically coupled to a drive controller 32 configured to perform a drive control.

Changes in the field current, for example, may control the drive power provided by first and second motor generators 4 and 5, more specifically, a rotational speed and a driving torque, which, hereinafter, may be also called a motor generator rotational speed and a motor generator torque. Moreover, each of first and second motor generators 4 and 5 is able to operate in regenerating mode, when it provides torque in a direction opposite to a direction of its rotation, to generate electrical power, so that the generated electrical energy may be used to charge the battery 21.

First planetary gear arrangement 8, as is well known in the art, includes a first sun gear 22, a first carrier 24, which carries first planetary gears 23, and a first ring gear 25. Second planetary gear arrangement 9 includes a second sun gear 26, a second carrier 28, which carries second planetary gears 27, and a second ring gear 29.

In this embodiment, the engine 2, first motor generator 4, second motor generator 5, first planetary gear arrangement 8 and second planetary gear arrangement 9 are all disposed on the same axis. First carrier 24 of first planetary gear arrangement 8 and second sun gear 26 of second planetary gear arrangement 9 are coupled together and connected drivably to the engine output shaft 3 of engine 2; first sun gear 22 of first planetary gear arrangement 8 is connected drivably to first rotor shaft 13 of first motor generator 4; second ring gear 29 of second planetary gear arrangement 9 is connected drivably to second rotor shaft 16 of second motor generator 5; first ring gear 25 of first planetary gear arrangement 8 and second carrier 28 of second planetary gear arrangement 9 are coupled together and connected to drive shafts 7 for traction wheels 6.

Drive connection to drive shaft 7 is accomplished, for example, by connecting an output portion 30 such as a gear formed on the outer circumference of first ring gear 25 of first planetary gear arrangement 8 to drive shaft 7 with output gearing 31. Drive connection of each of a portion of rotating elements of first planetary gear arrangement 8 to the corresponding one of rotating elements of second planetary gear arrangement 9 is accomplished directly without any power transmitting gear between them, and drive connection of each of the remainder of the rotating elements to the corresponding one of first motor generator 4, second motor generator 5 and engine 2 is accomplished similarly.

Now, collinear diagrams are used to describe relations, in rotational speed, between engine 2 or engine output shaft 3, first and second planetary gear arrangements (power split and composition system) 8 and 9, and output gearing 31.

As described before, first carrier 24 of first planetary gear arrangement 8 and second sun gear 26 of second planetary gear arrangement 9 are directly coupled together, and first ring gear 25 of first planetary gear arrangement 8 and second carrier 28 of second planetary gear arrangement 9 are directly coupled together. Therefore, first carrier 24 and second sun gear 26 turn at the same speed on collinear diagrams for two planetary gear arrangements 8 and 9, and first ring gear 25 and second carrier 28 turn at the same speed, too. Now, overlaying the two collinear diagrams for planetary gear arrangements 8 and 9 makes a collinear diagram, shown in FIG. 2, which has four vertical axes in total, that is, from the left, an axis for first sun gear 22 of first planetary gear arrangement 8 (an axis labeled "MG1" in FIG. 2: the first sun gear 22 being equivalent to first rotor shaft 13 of first motor generator 4), an axis for first carrier 24 of first planetary gear arrangement 8 and second sun gear 26 of second planetary gear arrangement 9 (an axis labeled "ENG" in FIG. 2: the first carrier 24 and second sun gear 26 being equivalent to the engine output shaft 3 of engine 2), an axis for first ring gear 25 of first planetary gear arrangement 8 and second carrier 28 of second planetary gear arrangement 9 (an axis labeled "OUT" in FIG. 2: first ring gear 25 and second carrier 28 being equivalent to output portion 30 of first ring gear 25, i.e. drive shaft 7 for traction wheel 6), and an axis for second ring gear 29 of second planetary gear arrangement 9 (an axis labeled "MG2" in FIG. 2: the second ring gear 29 being equivalent to second rotor shaft 16 of second motor generator 5). Then, a lever ratio indicative of the relation among the distances, each between the adjacent two of the vertical axes is found: assuming that the distance between the axes ENG and OUT is 1, the distance between the axes ENG and MG1 takes on the value k1 which results from dividing the number of teeth of first ring gear 25 of first planetary gear arrangement 8 by the number of teeth of first sun gear 22, the distance between the axes OUT and MG2 takes on the value k2 which results from dividing the number of teeth of second sun gear 26 of second planetary gear arrangement 9 by the number of teeth of second ring gear 29.

This collinear diagram for the power split and composition system is equivalent to what is previously proposed by the present Applicant in JP Patent No. 3852562. The characteristic of the power split and composition system is that the first motor generator 4 and the second motor generator 5 are located on one and the other points where the remotest two of the four vertical axes are. The relation in which the first and second motor generators 4 and 5 are placed on where the remotest two of the four vertical axes are provides not only, as mentioned in JP Patent No. 3852562, a configuration free from disadvantages such as an increase in number of parts, an increase in size of system, an increase of mechanical loss and so forth, but also, as will be described later, a reduction in the amount of an exchange of electrical energy during driving in ordinary situations with a high gear ratio, which in turn improves fuel efficiency.

Hereinafter, referring to several collinear diagrams, relations between speed and torque of the engine 2, travelling speed of the vehicle, speed and torque of the first and second motor generator 4 and 5 are described. In each of the collinear diagrams, Tmg1 is the first motor-generator torque provided by first rotor shaft 13 of first motor generator 4, Tmg2 is the second motor-generator torque by second rotor shaft 16 of second motor generator 5, Teng is the engine torque by the engine output shaft 3 of engine 2, Tout is the output drive torque from the output portion 30, i.e. the drive torque delivered to the drive shaft 7. In each of the collinear diagrams, it is defined that the rotational speed has a positive direction when the direction is the same as that of the engine 2 and the torque, as an input along each of the four axes, has a positive direction when the direction is the same as that of the engine torque Teng. Therefore, the driving torque Tout from the output portion 30 moves the vehicle backward when it has a positive direction and forward when it has a negative direction.

Although operation of a motor generator in the power running or regenerating mode is accompanied by losses which occur at an inverter and a motor generator during power generation so that the efficiency of energy conversion between electrical energy and mechanical energy is not 100%, it is hereinafter assumed that no mechanical, electrical and physical losses take place for simplicity of the following description. In case there is an actual need to take the losses into consideration, it is sufficient to perform a compensating control for the losses by, for example, generating more electrical power as much as the amount of energy lost as the losses.

Figure 2:
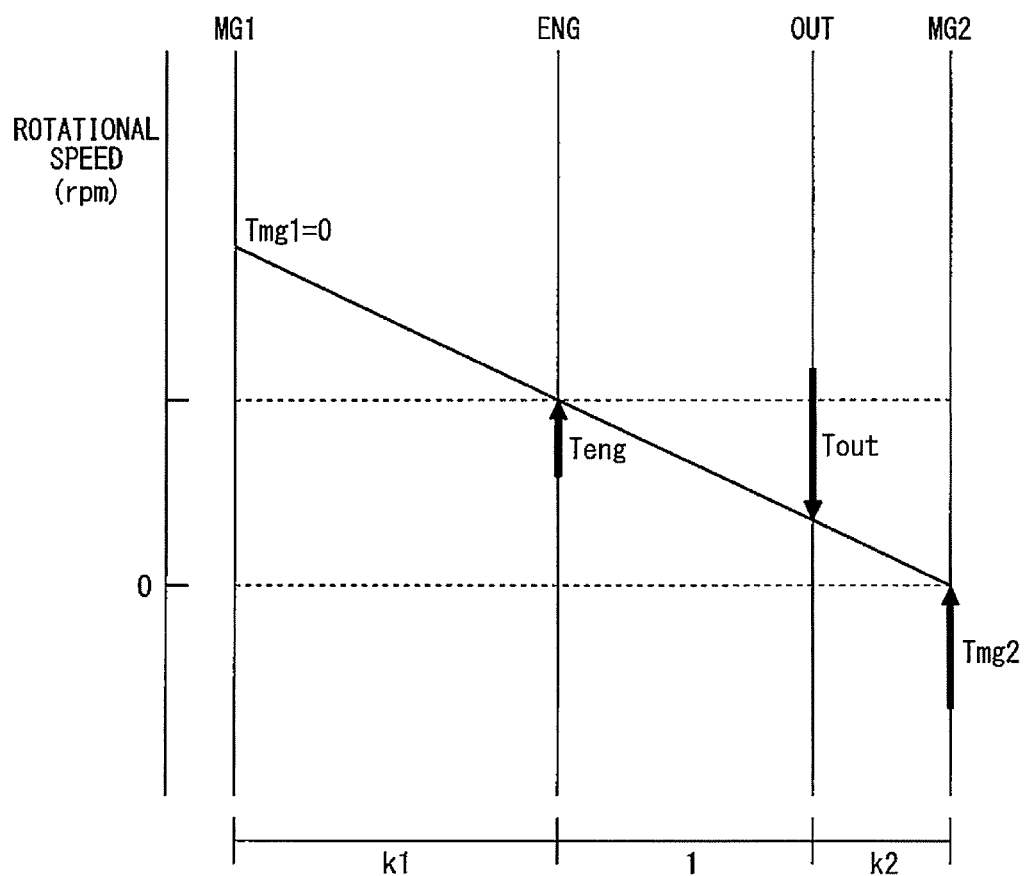
FIG. 2 shows an exemplary collinear diagram for a power split and composition system shown in FIG. 1.

FIG. 2 represents a low-speed drive state in which the vehicle speed (a driving speed of the vehicle) is relatively low and the engine (ENG) 2 turns in a positive rotational direction to provide a positive engine torque Teng. Although first motor generator (MG1) 4 turns in the positive rotational direction at a high speed, the first motor-generator torque Tmg1 remains 0. Although second motor generator (MG2) 5 provides a positive first motor-generator torque Tmg2, second motor generator (MG2) 5 does not consume electrical power because the second motor-generator rotational speed is 0 (operation out of power running mode). In this case, since a ratio of engine speed of the engine 2 to rotational speed of the output portion 30, i.e., vehicle speed, called "a gear ratio," is expressed as (1+k2)/k2, a state of low gear ratio is established because the transmission ratio is greater than 1.

Figure 3:
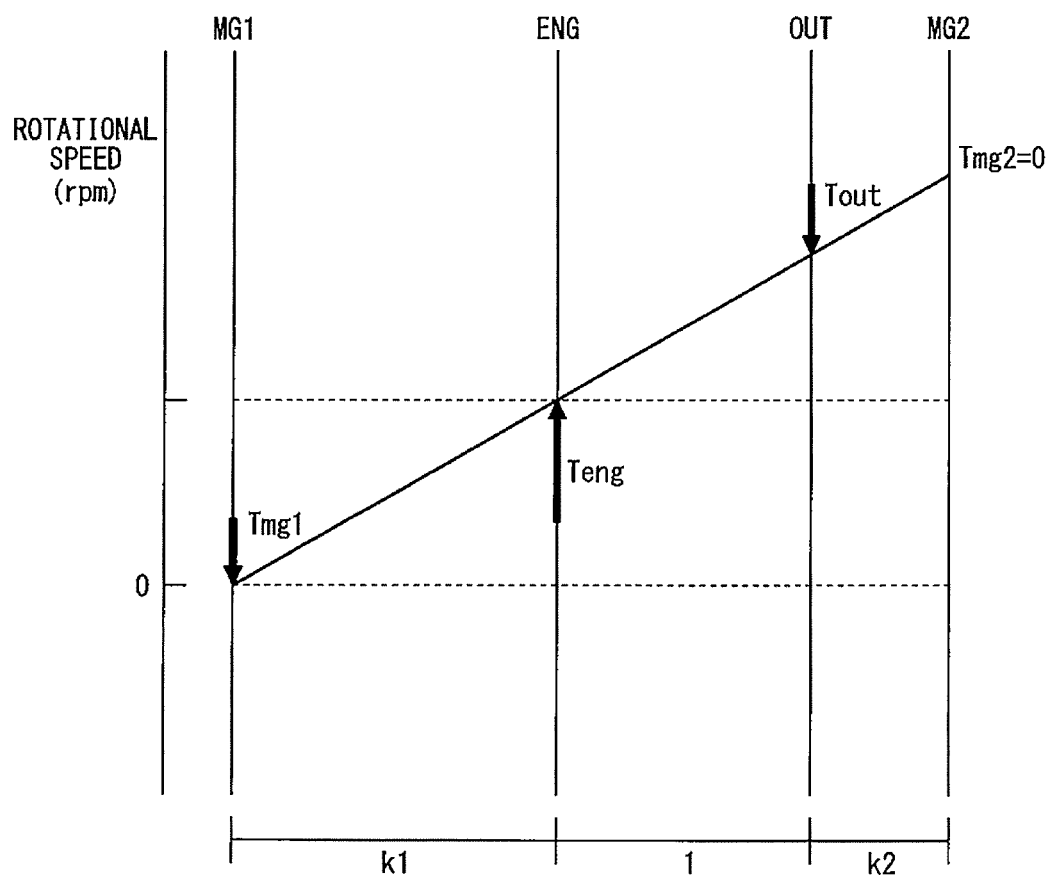
FIG. 3 shows an exemplary collinear diagram for the power split and composition system shown in FIG. 1.

FIG. 3 represents a high-speed drive state in which the vehicle speed Vc is relatively high and the engine 2 turns in the positive rotational direction to provide a positive engine torque Teng. Although first motor generator (MG1) 4 provides a negative first motor-generator torque Tmg1, first motor-generator (MG1) 4 does not generate electrical power because the first motor-generator rotational speed is 0 (operation out of regenerating mode). Although second motor generator (MG2) 5 turns in the positive rotational direction at a high speed, the second motor-generator torque Tmg2 remains 0. In this case, since a ratio of engine speed of the engine 2 to rotational speed of the output portion 30, i.e., vehicle speed, called "a gear ratio," is expressed as k1/(1+k1), a state of high gear ratio is established because the transmission ratio is less than 1.

Figure 4:
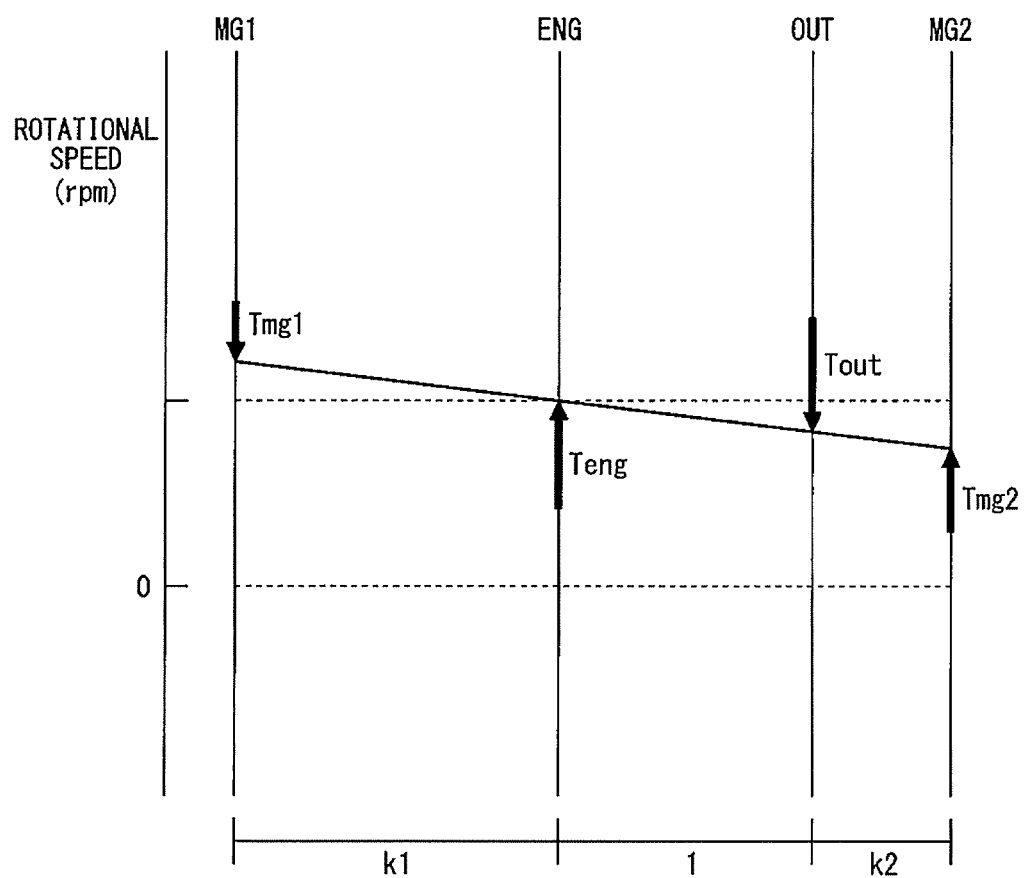
FIG. 4 shows an exemplary collinear diagram for the power split and composition system shown in FIG. 1.

FIG. 4 represents, for example, in the illustrated state, a middle-speed drive state, which corresponds to a state of intermediate gear ratio between the low gear ratio state of FIG. 2 and high gear ratio state of FIG. 3, in which the vehicle speed is middle and the engine 2 turns in a positive rotational direction to provide a positive engine torque Teng. First motor generator 4 turns in a positive rotational direction to provide a negative first motor-generator torque Tmg1. First motor generator 4 in fact generates electrical power (operation in regenerating mode). On the other hand, second motor generator 5 generates a positive second motor-generator torque Tmg2 though it turns in a positive rotational direction. Second motor generator 5 in fact is consuming electrical power (operation in power running mode). When there is no charge to or discharge from the battery 21, an exchange of electrical energy may be nicely balanced by powering second motor generator 5 with electrical power generated by first motor generator 4.

Thus, it is possible for the power split and composition system according to this embodiment to provide a suitable driving torque Tout to any one of various states of the engine operation by controlling the state of driving first motor generator 4 and the state of driving second motor generator 5 over a wide speed range from low speed to high speed. In principle, the hybrid electric vehicle according to this embodiment in fact does not need any transmission. Moreover, it is possible to drive the vehicle backward even when the engine 2 keeps running. It is also possible to drive the vehicle forward or backward when the engine 2 is shutdown by only both or one of first motor generator 4 and second motor generator 5. In this case, as JP Patent No. 3852562 describes, rotational speed of the engine 2 should be 0, and if a torque is imparted to the engine output shaft 3 in the negative direction, this torque would be received by a one-way clutch.

Figure 5:
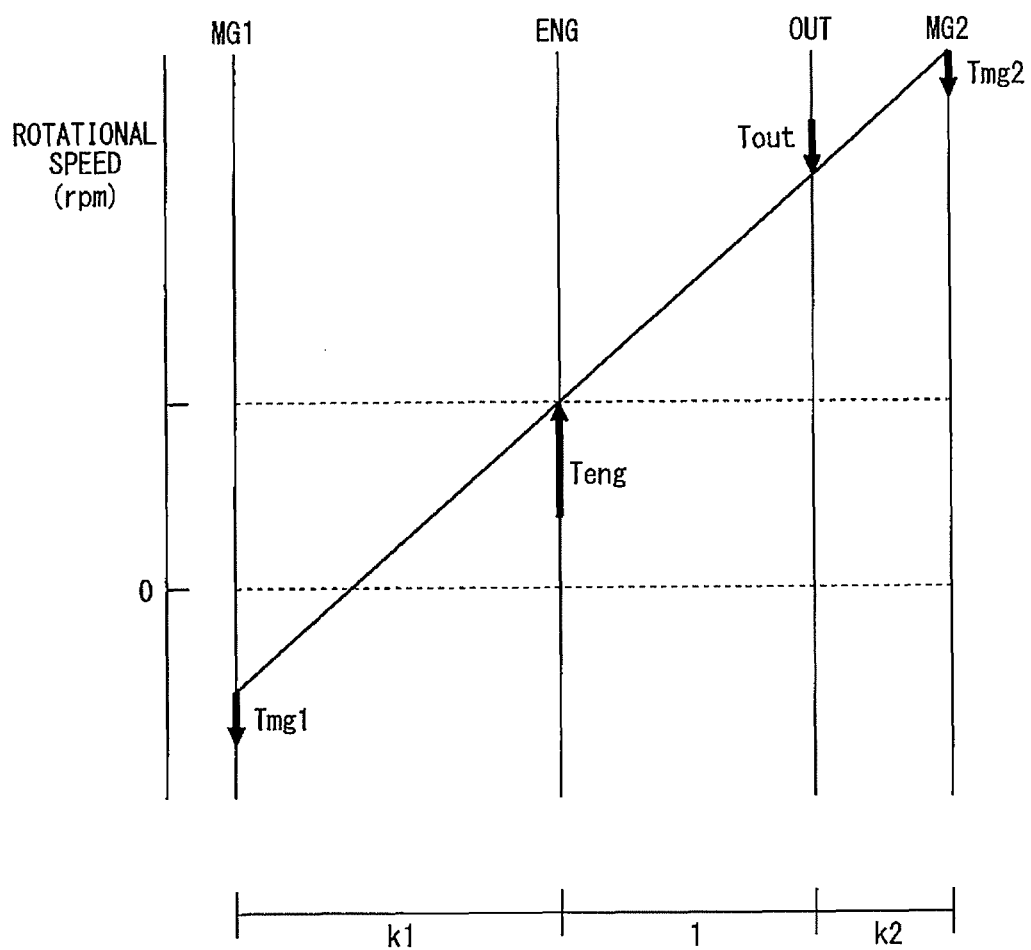
FIG. 5 shows an exemplary collinear diagram for the power split and composition system shown in FIG. 1.

FIG. 5 is a view illustrating power circulation through first and second motor generators 4 and 5. As shown in FIG. 5, in a drive state with a driving speed equal to or higher than the vehicle speed provided when the state of high gear ratio is established as represented by FIG. 3, the engine 2 turns in the positive rotational direction to provide a positive engine torque Teng. Then, the first motor generator 4 turns in the reverse rotational direction to provide a negative first motor-generator torque Tmg1. First motor generator 4 in fact consumes electrical power (operation in power running mode). On the other hand, although it turns in the positive rotational direction, the second motor generator 5 provides a negative second motor-generator torque Tmg2. The second motor generator 5 in fact generates electrical power (operation in regenerating mode). Operating first and second motor generators 4 and 5 in a way that one of them consumes electrical power (operation in power running mode) and the other generates electrical power (operation in regenerating mode) causes power circulation (circulation of power) to occur. Occurrence of such power circulation will reduce the efficiency of powertrain.

Turning back to the configuration of drive control apparatus 1, the engine 2 includes: an air quantity adjustment means 10, like a throttle valve, to adjust an air intake condition in response to the position of an accelerator pedal that is not illustrated; a fuel supply means 11, like a fuel injection valve, to adjust a fuel supply condition in response to the air intake condition; and an ignition means 12, like an ignition system, to adjust an ignition condition in response to ignition of fuel. The air quantity adjustment means 10, fuel supply means 11 and ignition means 12 are connected to a drive controller 32 configured to effect drive control.

According to such configuration, the state of burning fuel within the engine 2 is controlled by, for example, controlling the air intake condition by air quantity adjustment means 10, the fuel supply condition by fuel supply means 11 and the ignition condition by ignition means 12, resulting in control of drive power from the engine 2, specifically control of rotational speed and driving torque, which are hereinafter described as engine speed and engine torque. A one-way clutch, not illustrated, is provided to allow the engine output shaft 3 of engine 2 to turn in one direction only and prevent it from turning in the opposite direction.

Besides, the vehicle has an accelerator position sensor 33 configured to detect, as the accelerator position, the position of accelerator pedal, a driving speed sensor 34 configured to detect the vehicle speed, an engine speed sensor 35 configured to detect, as the engine speed, the rotational speed of the engine 2, and a battery state of charge sensor 36 configured to detect the amount of electrical energy stored at a battery 21, which may be referred to as the state of charge (SOC), a battery temperature detection sensor 37 configured to detect temperature of the battery 21, and a battery voltage detection sensor 38 configured to detect voltage of the battery 21.

The drive controller 32 reads the detection signals from these sensors and controls operating conditions of engine 2, first motor generator 4 and second motor generator 5 by controlling the air quantity adjustment means 10, fuel supply means 11, ignition means 12 and first and second inverters 19 and 20 in accordance with processing described later.

To perform such control, according to this embodiment, the drive controller 32 includes an engine control (or an operating point target calculation function) 40 configured to set up the efficient engine speed and torque for performing the control, and a motor generator control (or a motor torque command calculation function) 60 configured to control first and second inverters 19 and 20 so that the total power of first and second motor generators 4 and 5 may be made identical to the battery charge/discharge power target.

Incidentally, the drive controller 32 is built by a processor, like a microcomputer for example. Said set-up function and control function are built by processing steps performed in the drive controller 32.

(Functions Of Engine Control 40)

Figure 6:
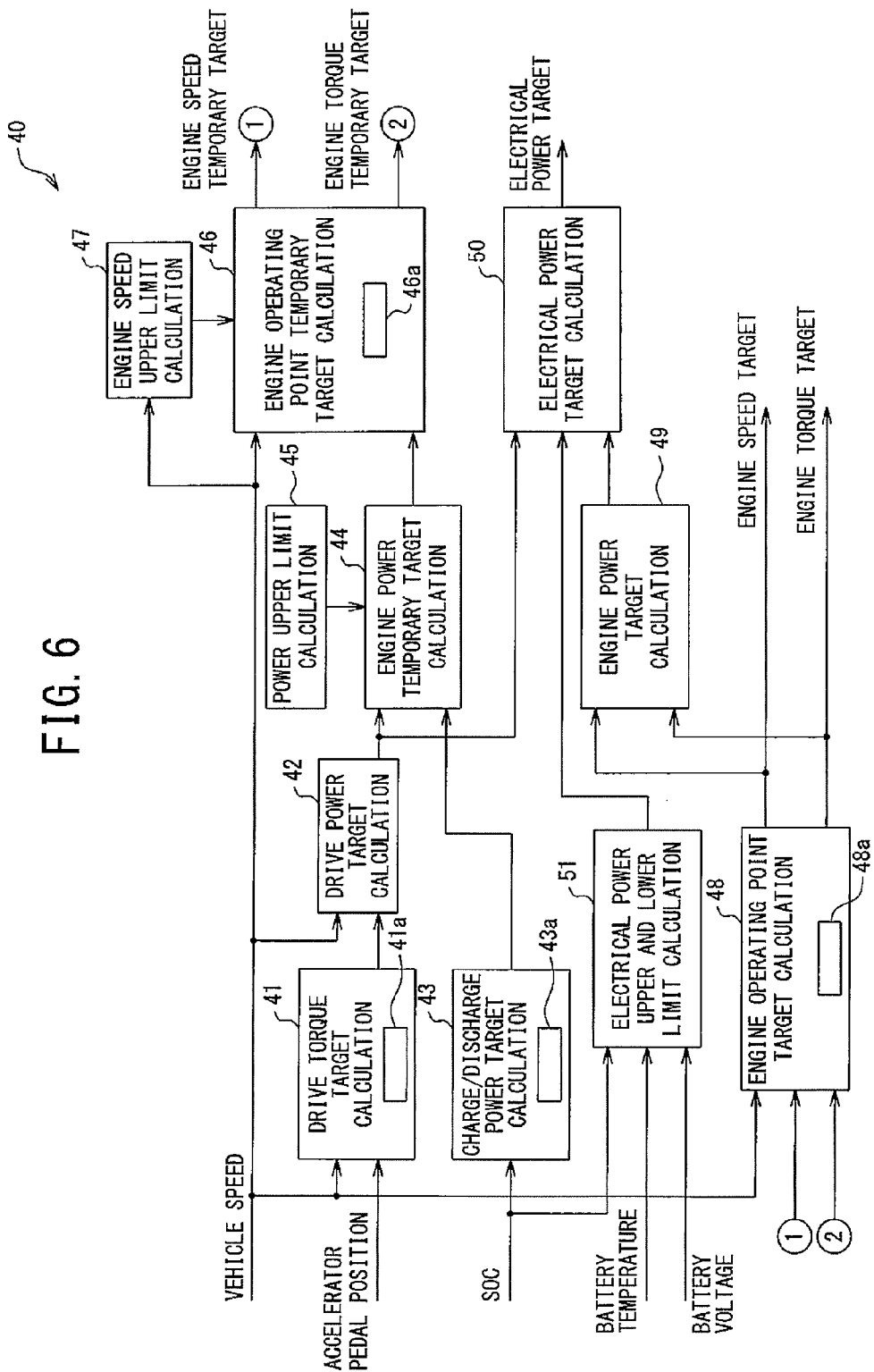
FIG. 6 is a functional block diagram showing an example of the functions of an engine control shown in FIG. 1.

FIG. 6 is a functional block diagram showing one example of functions of the engine control 40.

As shown in FIG. 6, the engine control 40 includes: a drive torque target calculation function 41; a drive power target calculation function 42; a charge/discharge power target calculation function 43; an engine power temporary target calculation function 44; a power upper limit calculation function 45; an engine operating point temporary target calculation function 46; an engine speed upper limit calculation function 47; an engine operating point target calculation function 48; an engine power target calculation function 49; an electrical power target calculation function 50; and an electrical power upper and lower limit calculation function 51.

Figure 7:
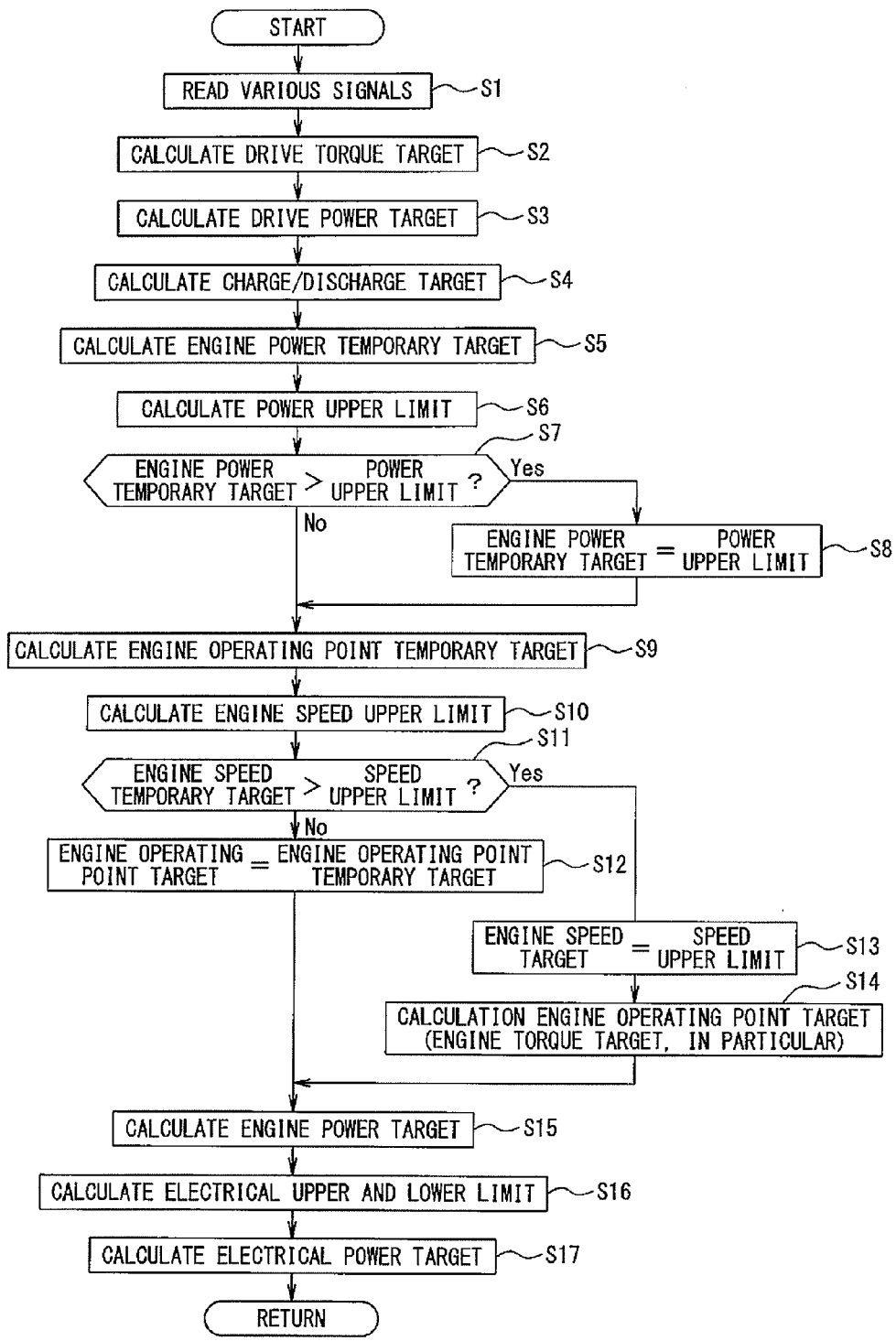
FIG. 7 is a flowchart representing an example of arithmetic processing performed in the engine control shown in FIG. 1.

FIG. 7 illustrates a routine for the engine control 40 which is implemented by the functions shown in FIG. 6. This routine may be executed, for example, in accordance with a processing strategy such as interrupt-driven using a timer to generate periodic interrupts, one upon elapse of a predetermined sampling time (for example, 10 msec.).

Referring to the routine of FIG. 7, a description on the content of processing implemented by each of the functions follows:

First, as shown in FIG. 7, at step S1, the engine control 40 reads various signals. In this embodiment, the engine control 40 reads such various signals from the accelerator position sensor 33, driving speed sensor 34, battery state of charge sensor 36, battery temperature detection sensor 37, and battery voltage detection sensor 38.

At the next step S2, the drive torque target calculation function 41 calculates a drive torque target (i.e., a vehicle propelling torque target). In this embodiment, the drive torque target calculating function 41 calculates a drive torque target in response to the vehicle speed and accelerator pedal position (which may be equivalent of the amount of depressing of the accelerator pedal) each of which has been read in said step S1. For example, the drive torque target calculation function 41 refers to a map 41a for retrieval of drive torque target to determine a drive torque target.

Figure 8:
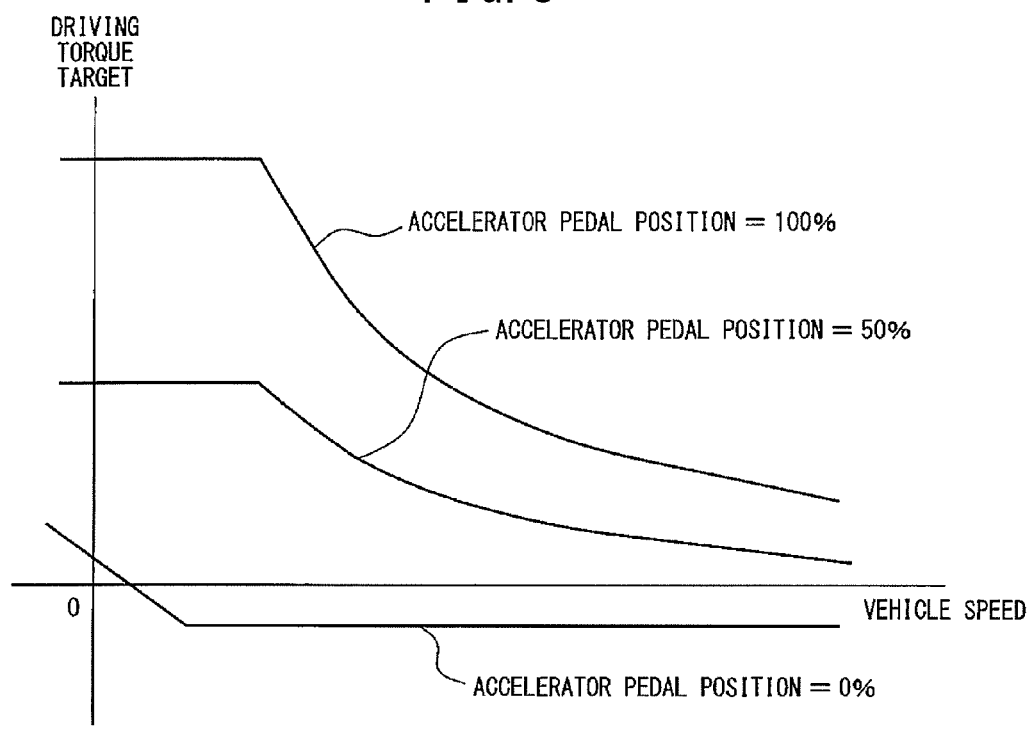
FIG. 8 shows an exemplary map used in the arithmetic processing shown in FIG. 7.

FIG. 8 illustrates an exemplary map 41a for retrieval of drive torque target.

As shown in FIG. 8, the map 41a for retrieval of drive torque target represents the relation among vehicle speed, drive torque target and accelerator pedal position. In the map 41a for retrieval of drive torque target, when the amount of depressing of the accelerator pedal is 0 in a range of high vehicle speeds, the drive torque target takes on a negative value to provide drive power in a direction tending to slow down the vehicle as effectively as engine braking might. In a range of low vehicle speeds, the drive torque target takes on one of positive values to allow the vehicle to keep rolling slowly ahead or creeping even when the accelerator pedal is released. It may be roughly said that, in the map 41a for retrieval of drive torque target, the less the accelerator pedal position angle, the less the drive torque target is, and the higher the vehicle speed, the less the drive torque target is.

The drive torque target calculation function 41 refers to the map 41a for retrieval of drive torque target to determine a drive torque target. The drive target calculation function 41 provides the determined drive target to the drive power target calculation function 42.

At the next step S3, the drive power target calculation function 42 calculates a drive power target indicative of the amount of power required for the amount of drive torque indicated by the drive torque target to propel the vehicle. Basically, in this embodiment, the drive power target calculation function 42 calculates the drive power target by multiplying the vehicle speed and the drive torque target calculated at said step S2. The setting of drive power target is such that, any of drive power targets falling in a band near the maximum of drive power stays greater than the power upper limit indicative of the maximum of power, later described, which the engine 2 is able to provide. The drive power target calculation function 42 provides the calculated drive power target to the engine power temporary target calculation function 44 and the electrical power target calculation function 50.

At the next step S4, the charge/discharge power target calculation function 43 calculates a charge/discharge power target (a charge/discharge amount target) in order to keep the state of charge (SOC) of the battery 21 within a range of ordinary use, that is, within a range from a predetermined upper limit to a predetermined lower limit. In this embodiment, the target charge/discharge power calculation function 43 refers to a charge/discharge amount target lookup table 43a to determine a corresponding value of the charge/discharge power target.

Figure 9:
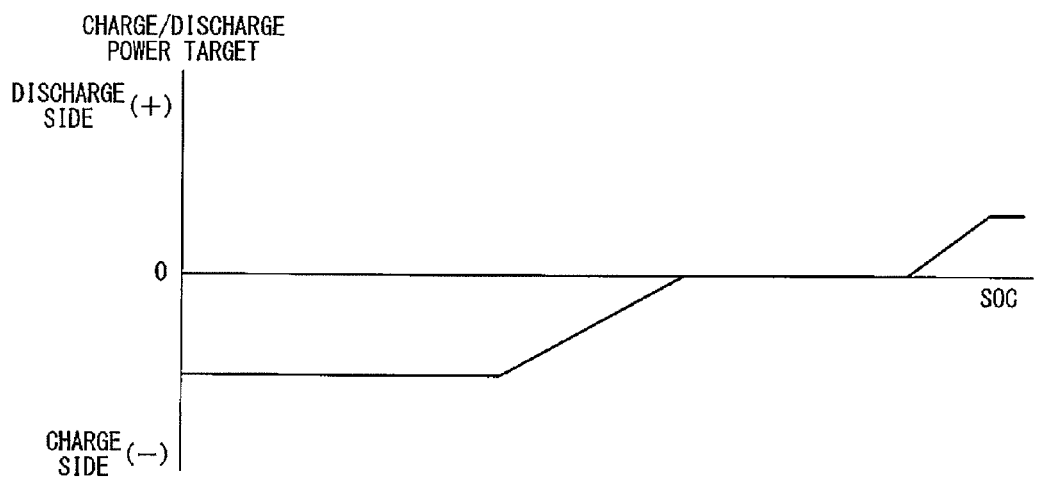
FIG. 9 is a graphical illustration of an exemplary lookup table used in the arithmetic processing shown in FIG. 7.

FIG. 9 shows an exemplary charge/discharge amount target lookup table 43a.

As shown in FIG. 9, the charge/discharge amount target lookup table 43a relates battery SOC to corresponding values of charge/discharge power target. In the charge/discharge amount lookup table 43a, when SOC is low, the charge/discharge power target takes on a value on the charge side in order to prevent over-discharge from the battery 21 by increasing charge power. Moreover, when the battery SOC is high, the charge/discharge power target takes on a value on the discharge side in order to prevent over-charge by increasing discharge power. In the target charge/discharge amount target lookup table 43a, the discharge side is positive and the charge side is negative for convenience.

The charge/discharge power target calculation function 43 refers to the charge/discharge amount target lookup table 43a to determine the charge/discharge power target. The charge/discharge power target calculation function 43 provides the determined charge/discharge power target to the engine power temporary target calculation function 44.

At the next step S5, the engine power temporary target calculation function 44 calculates an engine power temporary target indicative of the amount of power which the engine 2 is required to provide. In this embodiment, the engine power temporary target calculation function 44 calculates the engine power temporary target based on the drive power target calculated by the drive power target calculation function 42 at said step S3 and the charge/discharge power target calculated by the charge/discharge power target calculation function 43 at said step S4.

The engine power temporary target is a value resulting from the amount of power, which is required for propelling the vehicle, as modified by taking the amount of charge/discharge power for the battery 21 into consideration (by addition during battery charging, operation in regenerating mode, or subtraction during battery discharging, operation in power running mode). For example, in this embodiment, as the discharge side is negative, the engine power temporary target calculation function 44 subtracts the charge/discharge power target from the drive power target during battery discharging (operation in power running mode) to determine the engine power temporary target.

At the next step S6, the power upper limit calculation function 45 calculates a power upper limit indicative of an output maximum value which the engine 2 is able to provide. The setting is such that the power upper limit is a value determined experimentally or empirically or theoretically. Since this power upper limit is less than the maximum of the drive power target or the neighboring drive power target set up at said step S3, there occurs an operating state with a power assist by electrical power from the battery 21. For example, when the accelerator pedal is depressed to nearly 100%, the drive power target grows larger, and the operating state with power assist occurs easily.

The power upper limit calculation function 45 provides the calculated power upper limit to the engine power temporary target calculation function 44.

At the next step S7, the engine power temporary target calculation function 44 determines whether or not the calculated engine power temporary target is greater than the power upper limit.

If the engine power temporary target calculation function 44 determines that the engine power temporary target is greater than the power upper limit (engine power temporary target>power upper limit), the routine proceeds to step S8. However, if the engine power temporary target calculation function 44 determines that the engine power temporary target is less than or equal to the power upper limit (engine power temporary target≤upper limit), the routine proceeds to step S9.

At step S8, the engine power temporary target calculation function 44 sets the engine power temporary target to the power upper limit (engine power temporary target=power upper limit). Then, the engine power temporary target calculation function 44 allows the routine to proceed to step S9.

According to such steps S7 and S8, the engine power temporary target 44 places the engine power temporary target under upper limit guard. Then, the engine power temporary target 44 provides the engine power temporary target which has been calculated at step S8 (=power upper limit) or the engine power temporary target which has been calculated at step S5 power upper limit) to the engine operating point temporary target calculation function 46.

At step S9, the engine operating point temporary target calculation function 46 calculates an engine operating point temporary target (an engine speed temporary target and an engine torque temporary target). In this embodiment, the engine operating point temporary target calculation function 46 calculates the engine operating point temporary target based on the vehicle speed and the engine power temporary target which has been calculated by the engine operating point temporary target calculation function 46. In concrete terms, the engine operating point temporary target calculation function 46 refers to a map 46a for retrieval of engine operating point target to determine the engine operating point temporary target. The engine operating point temporary target calculation function 46 provides the engine operating point temporary target (engine speed temporary target and engine torque temporary target) to the engine operating point target calculation function 48.

Figure 10:
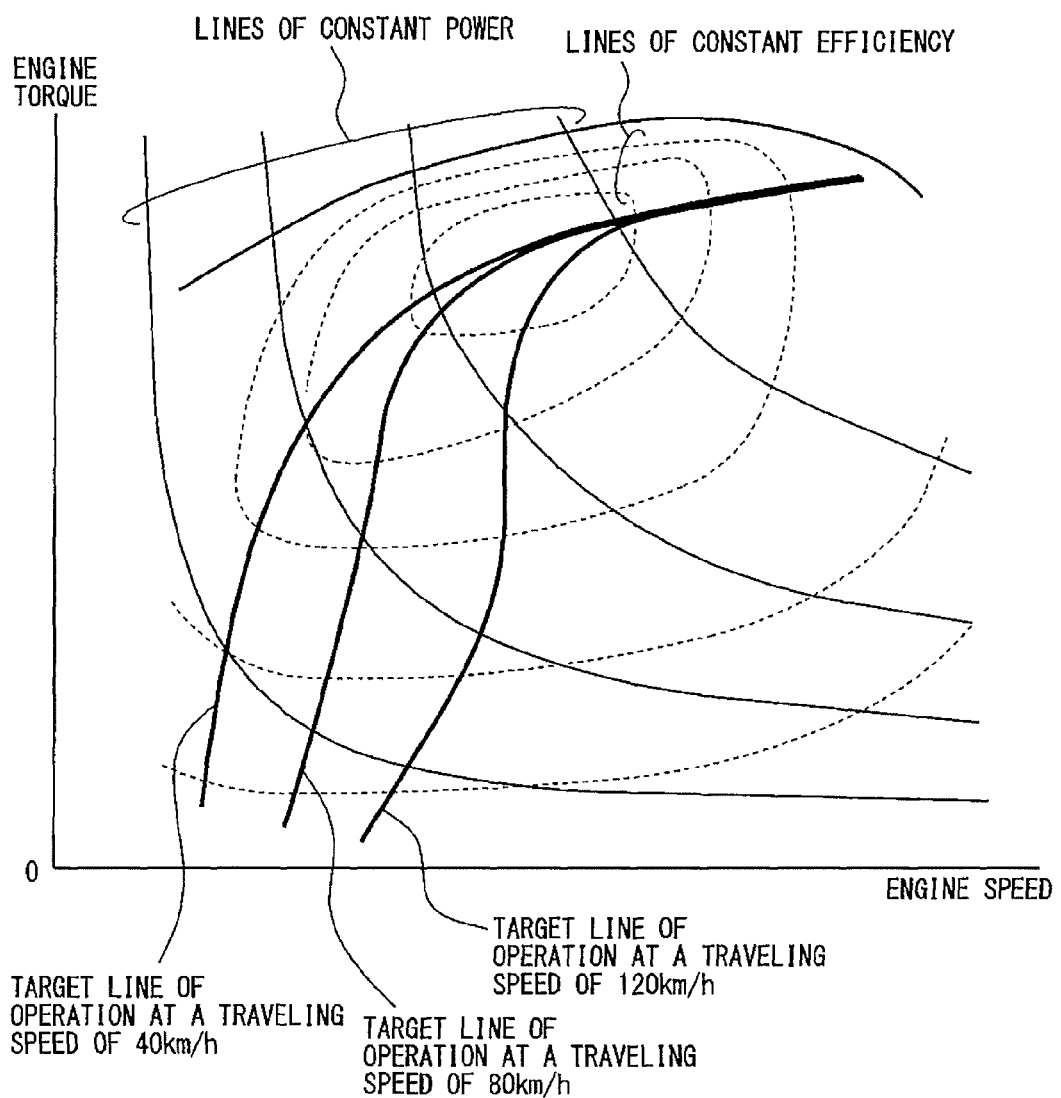
FIG. 10 is a graphical illustration of an exemplary engine characteristic diagram as a control map for retrieval of engine operating point.

FIG. 10 illustrates an exemplary map 46a for retrieval of engine operating point target.

As shown in FIG. 10, the map 46a for retrieval of engine operating point target represents the relation among engine speed (engine speed target), engine torque (engine torque target) and vehicle speed. In the map for retrieval of engine operating point target, the engine operating point target varies in response to the vehicle speed, and overall the higher the vehicle speed, the higher the engine speed and the lower the engine torque.

Figure 11:
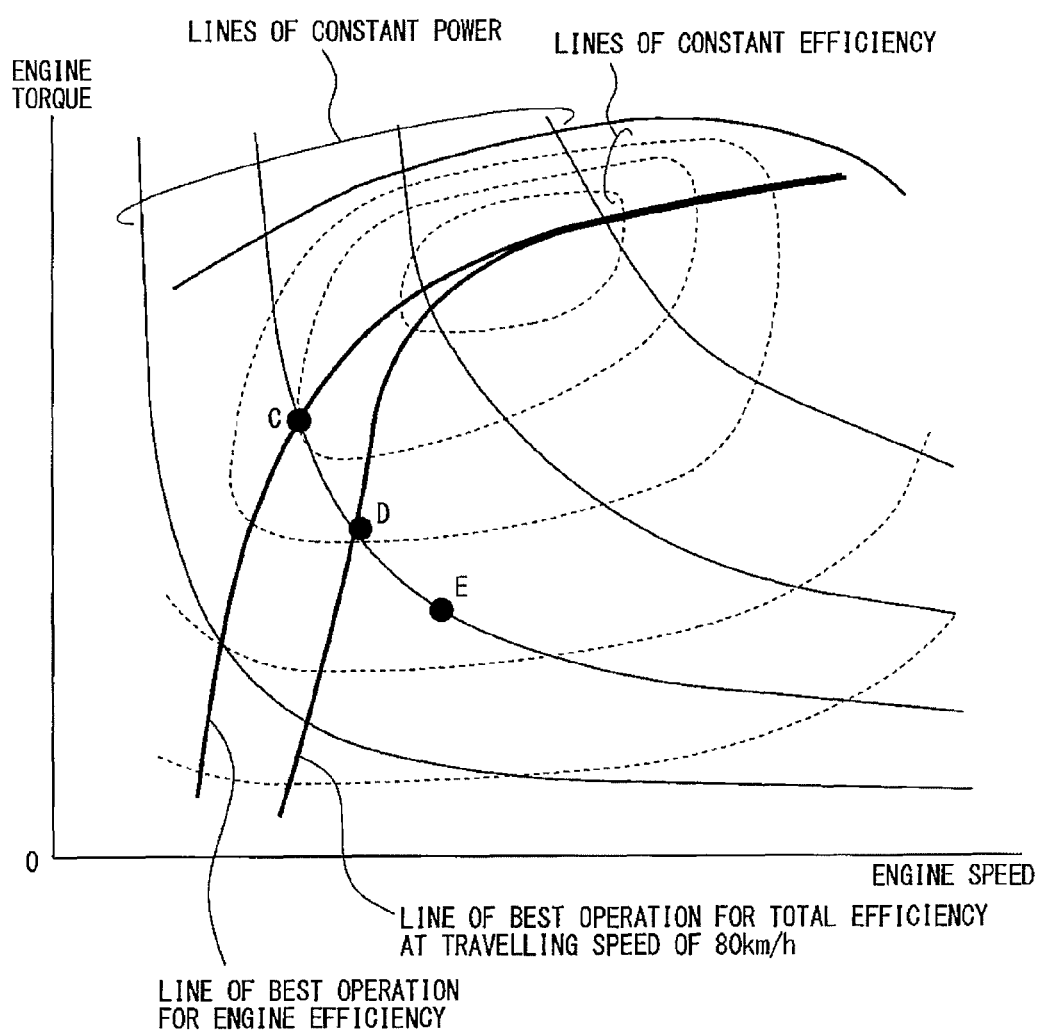
FIG. 11 is a graphical illustration of an exemplary engine characteristic diagram used to depict engine operating points and lines of the engine operation.

The reason that the map 46a for retrieval of engine operating point has been set is as follows:

Since the engine power is the product of engine speed and engine torque, lines of constant power of the engine power are inverse proportions in form when they are drawn in such a figure as shown in FIG. 11 with the horizontal axis representing engine speed and the vertical axis engine torque. In a characteristic diagram for the engine, there are lines of constant efficiency, each resulting from connecting points of constant efficiency after a function test of the engine. If, for example, the most efficient engine speed and torque are given out of that one of the lines of constant power which is selected for an engine power target which is set as a target to be achieved, it is possible to achieve driving with low fuel consumption, at least efficient function operation of the engine. Connecting these operation points make a line of best operation for engine efficiency as shown in FIG. 11.

The engine speed target and engine torque target which have been set in the above mentioned manner are now represented by an operating point C.

Figure 12:
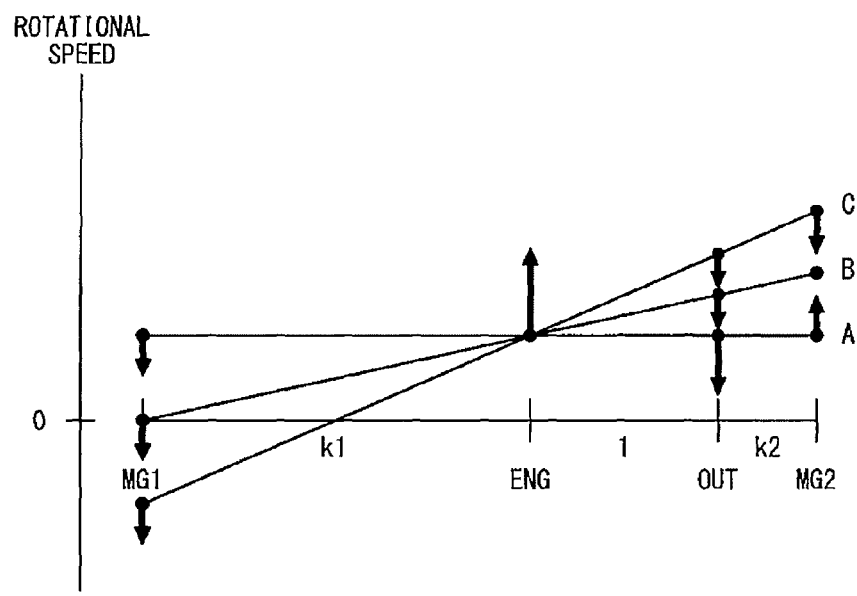
FIG. 12 shows an exemplary collinear diagram for the power split and composition system shown in FIG. 1.

With the engine speed target and the engine torque target set in this manner and fixed, the vehicle speed, i.e. the rotational speed of the output portion, is allowed to vary as shown in FIG. 12. In that case, since the vehicle speed is low and the rotational speed of the output portion is low, both of the first motor generator speed and the second motor generator speed are positive, and the first motor generator torque takes on a positive value and the second motor generator torque takes on a negative value as depicted with a collinear diagram A in FIG. 12. In this case, although the first motor generator 4 operates in regenerating mode and the second motor generator 5 in power running mode, since the rotational direction of both of them is the positive rotational direction, no power (motive power) circulates.

Similarly, when the vehicle speed takes on a value slightly higher (40 km/h, for example) and the output rotational speed also takes on a slightly higher value, the first motor generator rotational speed is 0, the first motor generator torque takes on a positive value, the second motor generator rotational speed is positive and the second motor generator torque is 0 as depicted with a collinear diagram B in FIG. 12 (same as the state of high gear ratio shown in said FIG. 3). In this case also, no power (motive power) circulates.

However, when the vehicle speed takes on a still higher value (80 km/h, for example) and the output rotational speed takes on a higher value accordingly, the first motor generator rotational speed takes on a negative value, the first motor generator torque takes on a negative value, the second motor generator rotational speed takes on a positive value and the second motor generator torque takes on a negative value as depicted with a collinear diagram C in FIG. 12. In this state, since the first motor generator 4 operates in power running mode in the negative rotational direction and the second motor generator 5 in regenerating mode, power (motive power) circulates, causing the efficiency of the powertrain to reduce. With the reduction in the efficiency of the powertrain, although the efficiency of the engine is high, the overall efficiency reduces and the efficiency at the operating point C is lower than that at an operating point D.

Figure 13:
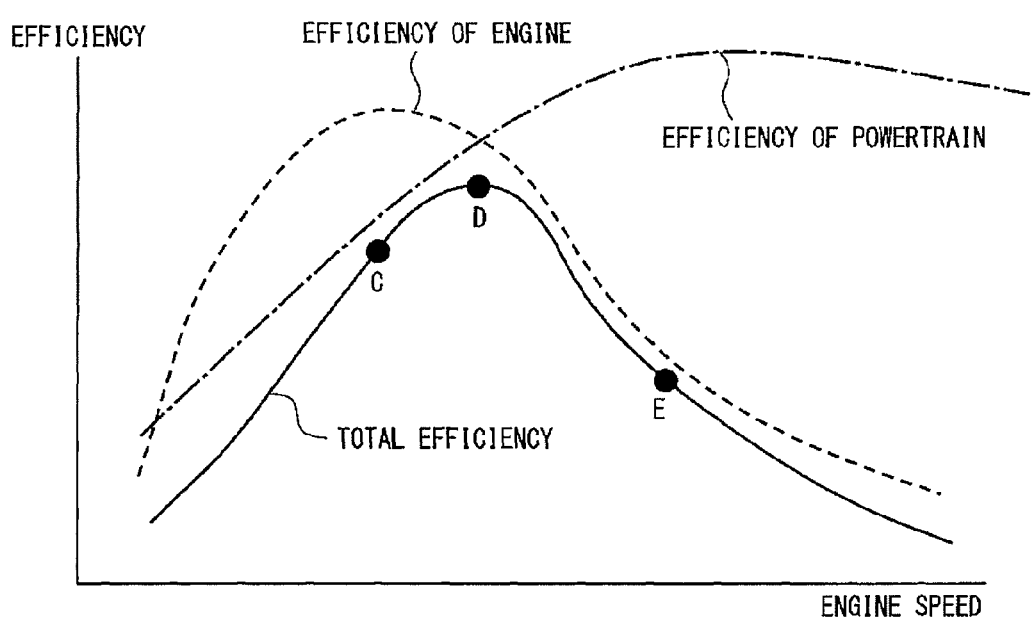
FIG. 13 is a graphical illustration showing an exemplary relation between engine speed and efficiency.
Figure 14:
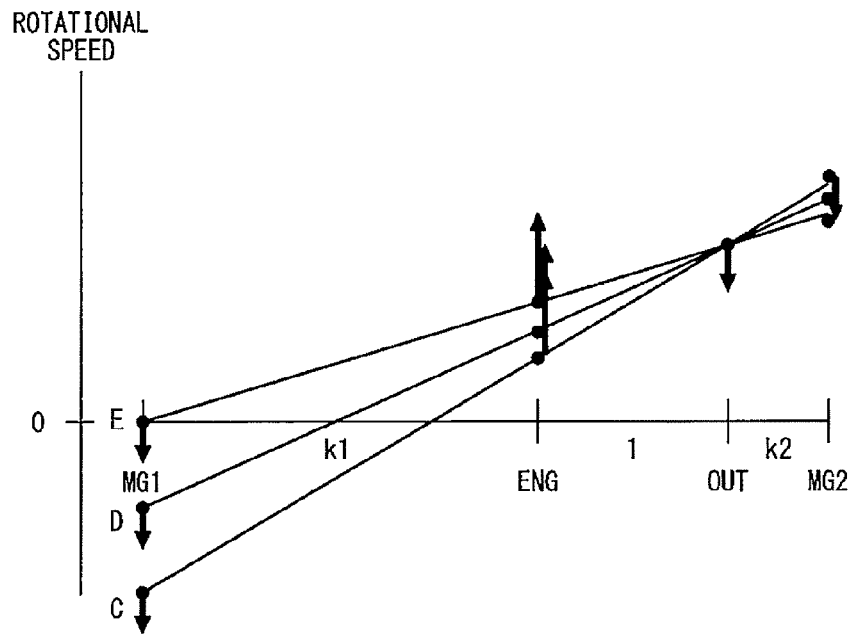
FIG. 14 shows an exemplary collinear diagram for the power split and composition system shown in FIG. 1.

Making the first motor generator rotational speed higher than or equal to 0, as depicted with a collinear diagram E in FIG. 14, may be considered as one approach to prevent power from circulating during driving at such high speed (80 km/h, for example), but this approach causes an increase in engine speed. If there is such increase in engine speed, the overall efficiency reduces though the efficiency of the powertrain is high as depicted at a point E in FIG. 13.

Then, for driving at such high speed (80 km/h, for example), the rotational speed of the engine is set to a point D lying between the point C and the point E as shown in FIG. 13 (see a collinear diagram D in FIG. 14). Referring to FIG. 11, this rotational speed of the engine at this operating point D is used as an engine speed target and an engine torque on the line of constant power for the engine power target versus the engine speed target is used as an engine torque target.

For those reasons, when, for example, an engine power target is set, the target operating lines vary with different values of driving speed to provide a setting that, overall, the higher the vehicle speed, the higher the engine speed target and the lower the engine torque target as shown in FIG. 10.

At the next step S10, the engine speed upper limit calculating function 47 calculates an engine speed upper limit (an upper limit of engine speed). In the present embodiment, the engine speed upper limit calculating function 47 calculates the engine speed upper limit based on the vehicle speed.

Figure 15:
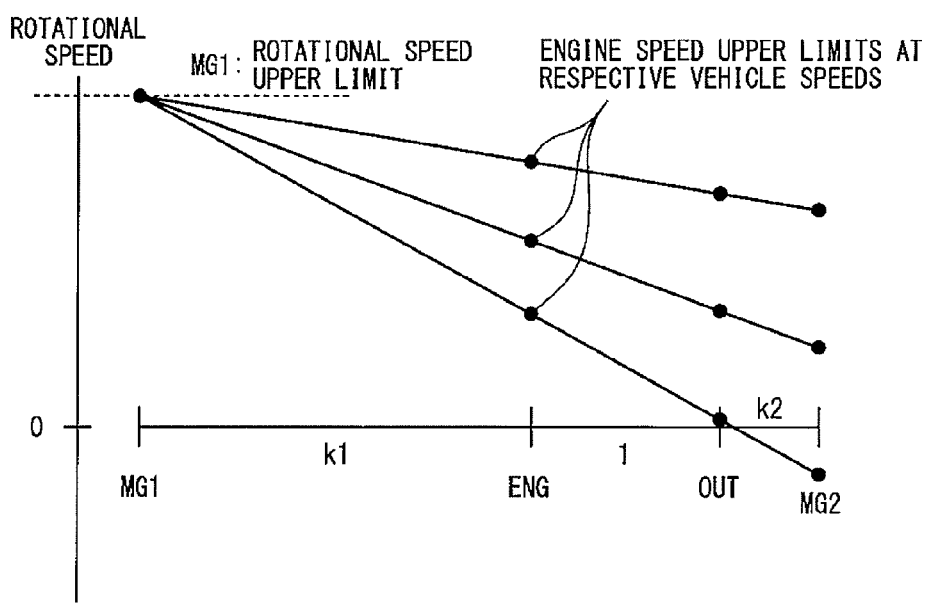
FIG. 15 shows an exemplary collinear diagram for the power split and composition system shown in FIG. 1.

FIG. 15 shows a collinear diagram illustrating the relation among a rotational speed upper limit of first motor generator 4, a rotational speed upper limit of engine 2, and a vehicle speed.

As shown in FIG. 15, the rotational speed upper limit of engine 2 is limited by the rotational speed upper limit of first motor generator 4. Moreover, the rotational speed of engine 2 should take on the value which depends on the vehicle speed (the rotational speed of a drive shaft). Under such relation, the engine operating point target calculation function 48 calculates the engine speed upper limit based on the vehicle speed, more concretely, based on the vehicle speed and the rotational speed upper limit of first motor generator 4.

At the next step S11, the engine operating point target calculation function 48 compares the engine speed temporary target to the engine speed upper limit determined at step S10 to determine whether or not the engine speed temporary target is greater than the engine speed upper limit. The engine operating point target calculation function 48 allows the routine to proceed to step S13 if it determines that the engine speed temporary target is greater than the engine speed upper limit (engine speed temporary target>engine speed upper limit). The engine operating point target calculation function 48 allows the routine to proceed to step S12 if it determines that the engine speed temporary target is less than or equal to the engine speed upper limit (engine speed temporary target≤engine speed upper limit).

At step S12, the engine operating point target calculation function 48 uses the engine operating point temporary point (engine speed temporary target and engine torque temporary target) just as it is as a set point of the engine operating point target (engine speed target and engine torque target), (engine operating point target=operating point temporary target). Then, the engine operating point target calculation function 48 allows the routine to proceed to step S15.

At step S13, the engine operating point target calculation function 48 sets the engine speed target to the engine speed upper limit (engine speed target=engine speed upper limit).

At the next step S14, the engine operating point target calculation function 48 calculates an engine torque target. In this embodiment, the engine operating point target calculation function 48 refers to a map 48a for retrieval of engine operating point target, which is similar to the map held by the engine operating point temporary target calculation function 46, to calculate an engine torque target versus the engine speed target (engine speed upper limit) set at said step S13. Then, the engine operating point target calculation function 48 allows the routine to proceed to step S15.

The engine operating point target calculation function 48 calculates (steps S12 to S14) an engine operating point target (engine speed target and engine torque target) to provide the calculated engine operating point target to the engine power target calculation function 49 and the motor generator control 60.

At step S15, the engine power target calculation function 49 calculates an engine power target. In this embodiment, the engine power target calculation function 49 calculates an engine power second target based on the engine operating point target (engine speed target and engine torque target) calculated by the engine operating point target calculation function 48.

If, now, the engine speed temporary target exceeds the engine speed upper limit (when it is determined that the answer to step S7 is "Yes"), the engine power target calculated at said step S15 takes on a value less than the engine power temporary target calculated by the engine power temporary target calculation function 44, i.e. the value at which the engine is able to produce power practically. If, on the other hand, the engine speed temporary target is equal to or less than the engine speed upper limit (when it is determined that the answer to step S7 is "No"), the engine power target calculated at said step S15 takes on a value equal to the engine power temporary target calculated by the engine power temporary target calculation function 44.

The engine power target calculation function 49 provides the calculated engine power target to the electrical power target calculation function 50.

At the next step S16, the electrical power upper and lower limit calculation 51 calculates an electrical power upper limit and an electrical power lower limit based on the entered battery temperature, battery voltage, and SOC. In the embodiment, the electrical power upper and lower limit calculation function 51 has electrical power upper and lower limit lookup tables 49a, 49b and 49c, which are accessible by the battery temperature, battery voltage and battery SOC, respectively; and it refers to the electrical power upper and lower limit lookup tables to determine corresponding values of the electrical power limits versus battery temperature, battery voltage and battery SOC.

Figure 16:
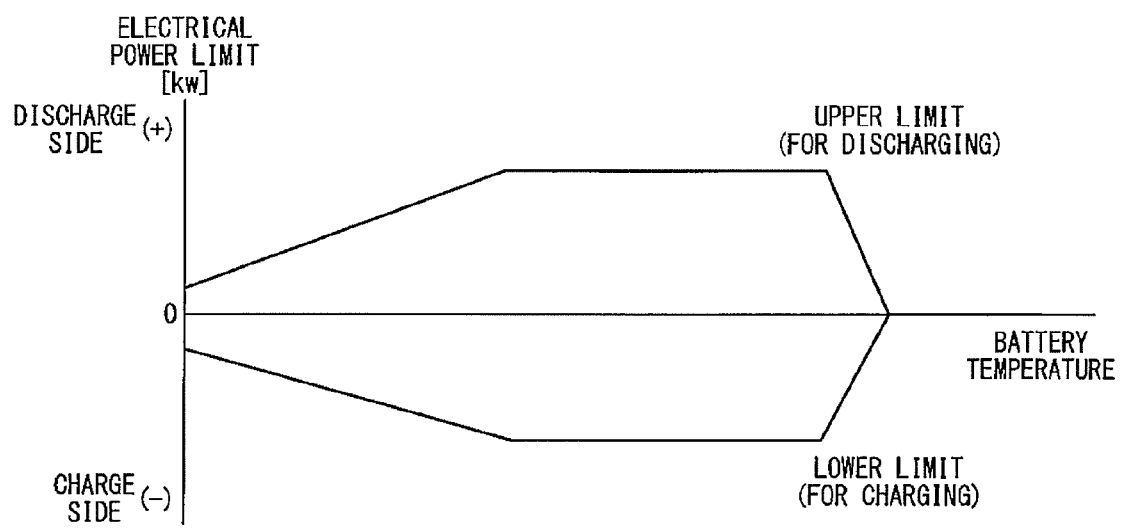
FIG. 16 shows an exemplary lookup table used in arithmetic processing shown in FIG. 7.
Figure 17:
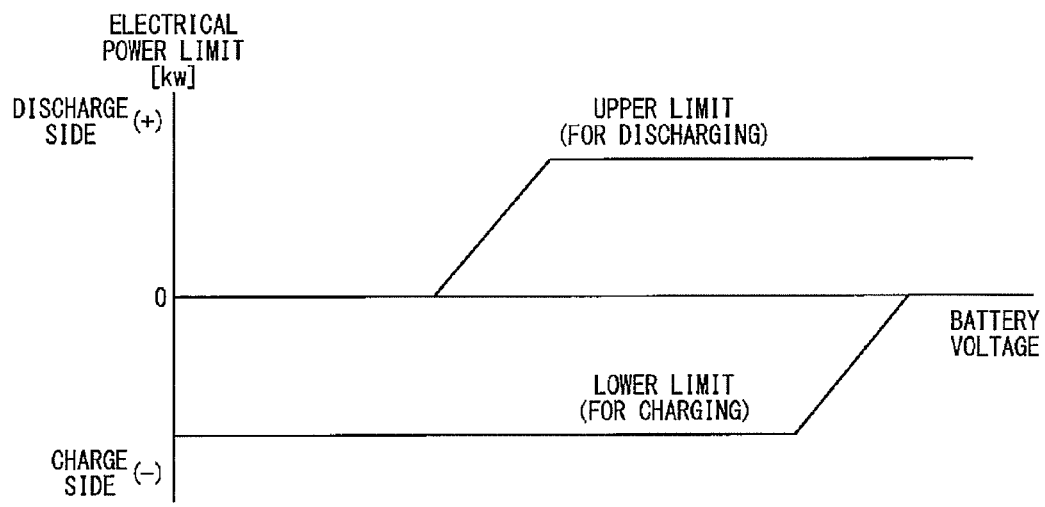
FIG. 17 shows an exemplary lookup table used in arithmetic processing shown in FIG. 7.
Figure 18:
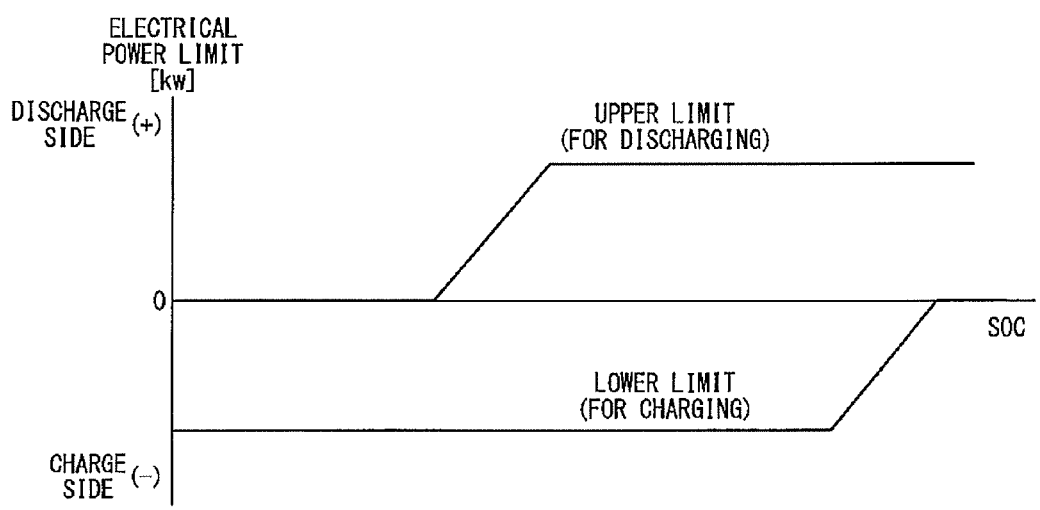
FIG. 18 shows an exemplary lookup table used in arithmetic processing shown in FIG. 7.

FIGS. 16, 17 and 18 depict exemplary electrical power upper and lower limit lookup tables 49a, 49b and 49c, respectively. FIG. 16 depicts an electrical power upper and lower limit lookup table 49a for relating battery temperature to corresponding values of electrical power limits, called hereinafter "a lookup table accessible by battery temperature". Moreover, FIG. 17 depicts an electrical power upper and lower limit lookup table 49b for relating battery voltage to corresponding values of electrical power limits, called hereinafter "a lookup table accessible by battery voltage". FIG. 18 depicts an electrical power upper and lower limit lookup table 49c for relating battery SOC to corresponding values of electrical power limits, called hereinafter "a lookup table accessible by battery SOC". In each of the electrical power upper and lower limit lookup tables 49*a*, 49*b* and 49*c*, the electrical power limits take on positive values for discharge side and negative values for charge side.

First, as shown in FIG. 16, in the lookup table accessible by battery temperature 49*a*, the absolute value of each of the electrical power limits on both of battery charging and discharging sides is small or 0 in an area where the battery temperature is low or high. This is because, when the battery temperature is low, reaction rate in the battery is slow and so the amount of electrical power which may be charged or discharged is reduced, and, when the battery temperature is high, a need arises to restrict the amount of electrical power for battery charging or discharging in order to prevent an excessive rise in battery temperature.

Moreover, as shown in FIG. 17, in the lookup table accessible by battery voltage 49*b*, the electrical power limit on battery discharging side is 0 in an area where the battery voltage is low. On the other hand, the electrical power limit of battery charging side is 0 in an area where the battery voltage is high.

This is because the battery deteriorates if it is used outside a range having voltage upper and lower limits which are set for the battery protection, and so there is a need to limit battery charging when the voltage is high and battery discharging when the voltage is low.

Moreover, as shown in FIG. 18, in the lookup table accessible by battery SOC 49*c*, the electrical power limit on battery discharging side is 0 in an area where the battery SOC is low. On the other hand, the electrical power limit on battery charging side is 0 in an area where the battery SOC is high. This is because it is necessary to avoid battery overcharge or overdischarge of SOC, and so there is a need to limit battery discharging when SOC is low and battery charging when SOC is high.

Turning, now, to FIG. 9, as the charge/discharge power target shows, the amount of power for battery charging is reduced when SOC is high in order to avoid overcharge, but this value is nothing more than an indication of the amount of electrical power to be generated by the engine power, and so the amount of power for battery charging is limited by the electrical power limit on charge side as shown in FIG. 18 in the case of battery charging by power generation in regenerating mode upon downhill driving.

On the other hand, if the drive torque requested by the vehicle driver requires a power assist and such power assist is implemented, the battery SOC is lowered depending on the amount of power consumed. If implementation of such power assist is frequently repeated, the battery SOC is gradually lowered because the power assist is implemented again before a loss in SOC is recovered. This is the case when the amount of electrical power on discharge side is limited.

Among electrical power limits on discharge side and those on charge side for battery temperature, battery voltage and SOC, which result from retrieval by referring to each of the above mentioned lookup tables 49*a*, 49*b* and 49*c*, the electrical power upper and lower limit calculation function 51 finally sets the minimum value selected from the electrical power limits on discharge side (i.e. electrical power upper limits on discharge side) for an electrical power upper limit, and finally sets the minimum value selected from the electrical power limits on charge side (i.e. electrical power upper limits on charge side) for an electrical power lower limit.

That is, among electrical power upper limits, one for battery charging and the other for battery discharging, obtained versus battery temperature by referring to the lookup table accessible by battery temperature 49*a*; electrical power upper limits, one for battery charging and the other for battery discharging, obtained versus battery voltage by referring to the lookup table accessible by battery voltage 49*b*; and electrical power upper limits, one for battery charging and the other for battery discharging, obtained versus SOC of battery 21 by referring to the lookup table accessible by battery SOC 49*c*, the electrical power upper and lower limit calculation function 51 evaluates each of the obtained upper limits according to how much an electrical power target is restricted to finally determine that one of the obtained upper limits for battery charging which has the greatest amount when the electrical power target is restricted and that one of the obtained upper limit for battery discharging which has the greatest amount when the electrical power target is restricted.

At the next step S17, the electrical power target calculation function 50 calculates an electrical power target so that it is restricted within a range defined between the electrical power upper and lower limits calculated at said step S15 by the electrical power upper and lower limit calculation function 51.

In the embodiment, the electrical power target calculation function 50 calculates an electrical power target by subtracting the engine power target from the drive power target.

The electrical power target means a target value of the amount of supply of electrical power to the battery 21 from first motor generator 4 and second motor generator 5 during operation in regenerating mode (charge of the battery 21) or the amount of supply of electrical power from the battery 21 to first motor generator 4 and second motor generator 5 during operation in power running mode (discharge from the battery 21), i.e. a target value of the amount of input/output electrical power to and from the battery 21. With regard to the relation between the drive power target and engine power target: when the drive power target is greater than the engine power target, the electrical power target means the amount of power-assist by the battery electrical power (supply of electrical power to first and second motor generators 4 and 5 from the battery 21). Since the engine power target means a value of power level at which the engine may produce power in practice, the drive torque requested by the vehicle driver may be provided by creating the amount of power assist in response to the calculated electrical power target. When the engine power target is greater than the drive power target, the electrical power target means the amount of electrical power which may be used to charge the battery 21.

Since, during battery charging (in regenerating mode), the engine power temporary target is the sum of the drive power target and the charge/discharge power target, when the engine speed temporary target is less than or equal to the engine speed upper limit and the engine power target is equal to the engine power temporary target, the electrical power target calculation function 50 calculates a value that is equal to the charge/discharge power target (the charge power target in this case) calculated at said step S4 as the electrical power target, i.e., the difference between the engine power target and the drive power target. On the other hand, when the engine speed temporary target is limited by the engine speed upper limit in a way not to exceed the engine speed upper limit and the engine power target is less than the engine power temporary target, the electrical power target calculation function 50 calculates, as the electrical power target, a value that is less than the charge/discharge power target (the charge power target in this case) calculated at said step S4. This means that the amount of charge power is reduced during battery charging (in regenerating mode).

On the other hand, during battery discharging (in power running mode), when the engine speed temporary target is less than or equal to the engine speed upper limit and the engine power target is equal to the engine power temporary target, the electrical power target calculation function 50 calculates, as the electrical power target, a value that is equal to the charge/discharge power target (the discharge power target in this case) calculated at said step S4. On the other hand, when the engine speed temporary target is limited by the engine speed upper limit in a way not to exceed the engine speed upper limit and the engine power target is less than the engine power temporary target, the electrical power target calculation function 50 calculates, as the electrical power target, a value that is greater than the charge/discharge power target (the discharge power target in this case) calculated at said step S4. This means that the amount of discharge power is increased during battery discharging (in power running mode).

The electrical power target calculation function 50 restricts the electrical power target calculated as mentioned before using the electrical power upper and lower limits. That is, the electrical power target calculation function 50 sets the electrical power target (in this case, the electrical power target for battery discharging) to the electrical power upper limit when the electrical power target exceeds the electrical power upper limit (electrical power target=electrical power upper limit), and sets the electrical power target (in this case, the electrical power target for battery charging) to the electrical power lower limit when the electrical power target is below the electrical power lower limit (electrical power target=electrical power lower limit).

The engine control 40 controls the state of air intake by the air quantity adjustment means 10, the state of fuel supply by the fuel supply means 11 and the state of ignition by the ignition means 12 in a way to achieve the calculated engine operating point target, especially the engine torque target.

(Functions of Motor Generator Control 60)

Figure 19:
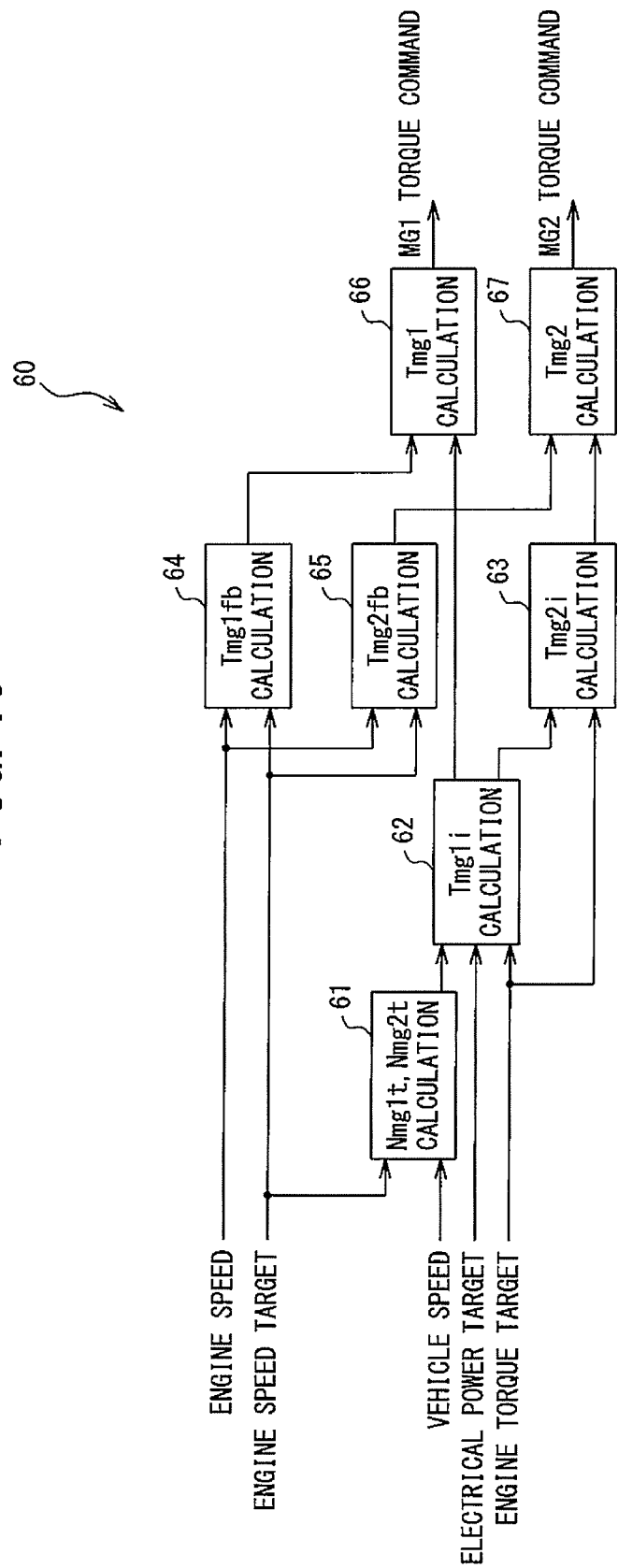
FIG. 19 is a functional block diagram showing an example of the functions of a motor generator control shown in FIG. 1.

FIG. 19 is a functional block diagram showing one example of functions of the motor generator control 60.

As shown in FIG. 19, the motor generator control 60 includes a motor speed calculation function (a Nmg1t and Nmg2t calculation function) 61, a first and a second base torque calculation function (a Tmg1i calculation function and a Tmg2i calculating function) 62 and 63, a first and a second feedback torque correction calculation function (a Tmg1fb calculation function and a Tmg2fb calculation function) 64 and 65 and a first and a second torque command calculation function (a Tmg1 calculation function and a Tmg2 calculation function) 66 and 67.

Figure 20:
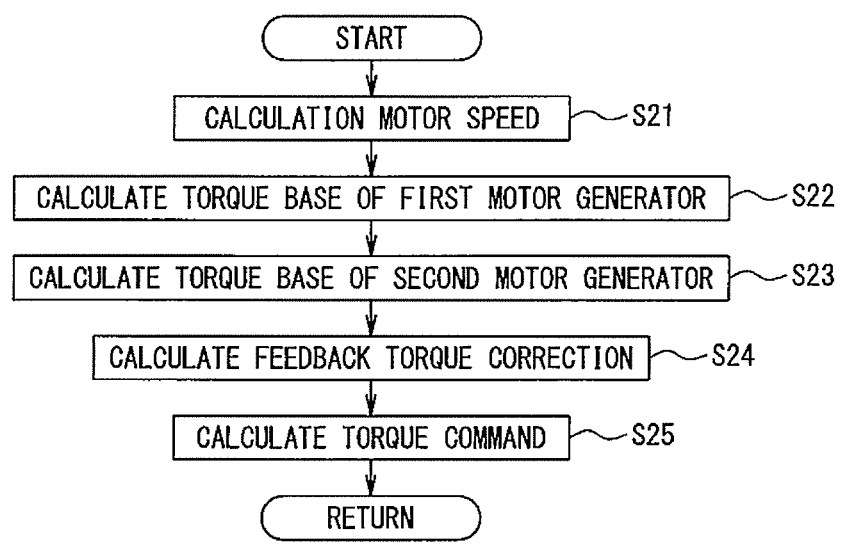
FIG. 20 is a flowchart representing an exemplary arithmetic processing performed in the motor generator control shown in FIG. 1.

FIG. 20 illustrates a routine for the motor generator control 60 which is implemented by the functions shown in FIG. 19. This routine may be executed, for example, in accordance with a processing strategy such as interrupt-driven using a timer to generate periodic interrupts, one upon elapse of a predetermined sampling time (for example, 10 msec.).

Referring to the routine of FIG. 20, a description on the content of processing implemented by each of the functions follows:

First, as shown in FIG. 20, at step S21, the motor speed calculation function 61 calculates the drive shaft rotational speed Nout, i.e. the rotational speed of the output portion 30 of the planetary gear arrangements, based on the vehicle speed. Thus, the output rotational speed Nout is derived from the vehicle speed, the differential gear ratio and the gear ratio of the output gearing 31.

The motor speed calculation function 61 calculates the rotational speed Nmg1t of the first motor generator 4 and the rotational speed Nmg2t of the second motor generator 5 when the engine speed takes on the engine speed target Neng. In the present embodiment, the motor speed calculation function 61 calculates first motor generator speed Nmg1t and second motor generator speed Nmg2t from equations (1) and (2) derived from the relation between rotational speeds of the planetary gear arrangements. The equations are as follows:

$$Nmg1t=(Neng-Nout)\cdot k1+Neng \qquad (1), \text{ and}$$

$$Nmg2t=(Nout-Neng)\cdot k2+Nout \qquad (2),$$

where: k1, k2 are the values resulting from ratios of the number of gears within the planetary gear arrangements, as mentioned before.

The motor speed calculation function 61 provides the calculated first and second motor speeds Nmg1t and Nmg2t to the first torque base calculation function 62.

At the next step S22, first torque base calculation function 62 calculates a first torque base for first motor generator 4. In this embodiment, first torque base calculation function 62 calculates first torque base Tmg1i for first motor generator 4 based on the electrical power target (the charge/discharge power target) Pbatt finally calculated by the engine control 40, first and second motor generator speeds Nmg1t and Nmg2t calculated at step S21 by the motor speed calculation function 61, and engine torque base Tengt calculated by the engine control 40. Concretely, first torque base calculation function 62 calculates torque base Tmg1i for first motor generator 4 from equation (3) as follows:

$$Tmg1i=(Pbatt\cdot 60/(2\cdot\pi)-Nmg2t\cdot Tengt/k2)/(Nmg1t+Nmg2t\cdot(1+k1)/k2) \qquad (3).$$

Equation (3) is obtained by solving simultaneous the following equations (4) and (5):

$$Tengt+(1+k1)\cdot Tmg1 = k2\cdot Tmg2 \qquad (4), \text{ and}$$

$$Nmg1\cdot Tmg1\cdot 2\cdot\pi/60+Nmg2\cdot Tmg2\cdot 2\cdot\pi/60=Pbatt \qquad (5).$$

Equation (4) is an equation expressing a balance of torque inputs to the planetary gear arrangements (a torque balance equation). That is, equation (4) balances torque target Tmg1 of first motor generator 4, torque target Tmg2 of second motor generator 5 and engine torque target Tengt based on the lever ratio derived from ratios in number of teeth of gears of the planetary gear arrangements, which mechanically couple first and second motor generators 4 and 5 to engine 2.

Equation (5) is an equation expressing a balance between the amount of electrical power generated or consumed by first motor generator 4 and second motor generator 5 and the amount of input/output electrical power, as indicated at Pbatt, to and from battery 21 (charge/discharge power), called a power balance equation.

First torque base calculation function 62 provides torque base Tmg1i to second torque base calculation function 63 and first torque command calculation function 66.

At the next step S23, second torque base calculation function 63 calculates torque base Tmg2i of second motor generator 5. In the present embodiment, the second torque base calculation function 63 calculates torque base Tmg2i of second motor generator 5 based on torque base Tmg1i calculated by first torque base calculation unit 62 at said step S22 and engine torque target Tengt calculated by the engine control 40. Concretely, the second torque base calculation function 63 calculates torque base Tmg2i of second motor generator 5 from the following equation (6):

$$Tmg2i=(Tengt+(1+k1)\cdot Tmg1i)/k2 \qquad (6).$$

This equation (6) is derived from said equation (4).

Second torque base calculation function 63 provides the calculated torque base Tmg2i of second motor generator 5 to second torque commanded calculation function 67.

At the next step S24, first and second feedback torque correction calculation functions 64 and 65 calculate respective feedback torque corrections Tmg1fb and Tmg2fb for first motor generator and second motor generators 4 and 5.

In this embodiment, first feedback torque correction calculation function 64 calculates feedback torque correction Tmg1fb for first motor generator 4 based on the engine speed and the engine speed target. Similarly, the second feedback torque correction calculation function 65 calculates the feedback torque correction Tmg2fb for second motor generator 5 based on the engine speed and the engine speed target.

Concretely, the first and second feedback torque correction calculation functions 64 and 65 calculate the respective feedback torque corrections Tmg1fb and Tmg2fb by multiplying the deviation of the measured value of the engine speed (the engine speed) from the target value (the engine speed target) by a predetermined feedback gain in order to bring the engine speed close to the engine speed target.

First and second feedback torque correction calculation functions 64 and 65 may provide feedback torque corrections Tmg1fb and Tmg2fb with relevance to ratios in number of teeth of gears of and the lever ratio of the planetary gear arrangements, which have four rotational elements coupled to first motor generator 4, second motor generator 5, drive shaft 7 and engine 2, respectively.

First feedback torque correction calculation function 64 provides the calculated feedback torque correction Tmg1fb for first motor generator 4 to first torque command calculation function 66. Second feedback torque correction calculation function 65 provides the calculated feedback torque correction Tmg2fb for second motor generator 5 to second torque commanded calculation function 67.

At the next step S25, first and second torque command calculation functions 66 and 67 calculate respective torque commands for first and second motor generators 4 and 5.

In the present embodiment, the first torque command calculation unit 66 calculates a torque command for first motor generator 4 based on the torque base Tmg1i for first motor generator 4 calculated by first torque base calculation function 62 at said step S22 and a feedback torque correction Tmg1fb for the first motor generator 4 calculated by first feedback torque correction calculation function 64 at said step S24. Similarly, the second torque command calculation function 67 calculates a torque command for second motor generator 5 based on the torque base Tmg2i for second motor generator 5 calculated by second torque base calculation function 63 at said step S23 and a feedback torque correction Tmg2fb for second motor generator 5 calculated by second feedback torque correction calculation function 65 at said step S24.

Concretely, first and second torque command calculation functions 66 and 67 calculate the torque commands for the respective motor generators 4 and 5 by adding the torque bases Tmg1i and Tmg2i to the feedback torque corrections Tmg1fb and Tmg2fb, respectively. That is, the first and second torque command calculation functions 66 and 67 set the respective feedback torque corrections so that the actual engine speed may converge to the engine speed target derived from the engine operating point target.

The motor generator control 60 provides the calculated torque commands Tmg1i and Tmg2i for first and second motor generators 4 and 5 to first and second inverters 19 and 20, respectively. First and second inverters 19 and 20 regulate first and second motor generators 4 and 5 based on the torque commands Tmg1i and Tmg2i, respectively. This causes first and second motor generators 4 and 5 to operate in power running mode or regenerating mode.

(Operation)

According to the drive control apparatus mentioned previously, a drive torque target is calculated in response to the vehicle speed and accelerator pedal position, and a charge/discharge power target is calculated together with calculating a drive power target based on the calculated drive torque target and the vehicle speed (step S1 through step S4). Then, the drive control apparatus calculates an engine power temporary target based on such calculated drive power target and charge/discharge power target (step S5). Moreover, the drive control apparatus keeps the calculated engine power temporary target unchanged when the calculated engine power temporary target is equal to or less than the power upper limit, and sets the engine power temporary target to the power upper limit when the engine power temporary target is greater than the power upper limit (step S6 through step S8).

The drive control apparatus calculates an engine operating point temporary target (an engine speed temporary target and an engine torque temporary target) by referring to the map for retrieval of engine operating point target based on the engine power temporary target that is kept unchanged or set to the power upper limit and vehicle speed (step S9). On the other hand, the drive control apparatus calculates an engine speed upper limit based on the vehicle speed, and compares such calculated engine speed temporary target to the calculated engine speed upper limit (step S10, step S11). This enables the drive control apparatus to set the engine operating point that remains unchanged as an engine operating point target when the engine speed temporary target is equal to or less than the engine speed upper limit, and the drive control apparatus is enabled to set the engine speed upper limit as an engine speed target when the engine speed temporary target is greater than the engine speed upper limit and then to refer to the map for retrieval of engine operating point target to recalculate an engine torque target versus the set engine speed target (the engine speed upper limit), (step S12 through step S14).

The drive control apparatus calculates an engine power target based on the engine operating point target (the engine speed target and engine torque target), (step S15), and calculates an electrical power target by subtracting such calculated engine power target from the drive power target (step S16).

During battery charging (in regenerating mode), an electrical power target is calculated as follows:

When an engine speed temporary target is equal to or less than an engine speed upper limit and an engine power target is equal to an engine power temporary target, the drive control apparatus calculates an electrical power target that is equal to a charge/discharge power target (a charge power target, in this case). On the other hand, when, in order for an engine speed temporary target not to exceed an engine speed upper limit, the engine power temporary target is limited by and thus equal to the engine speed upper limit, and an engine power target is less than an engine power temporary target, the drive control apparatus calculates an electrical power target that is equal to a value less than a charge/discharge power target (a charge power target, in this case).

During battery discharging (in power running mode), an electrical power target is calculated as follows:

When an engine speed temporary target is equal to or less than an engine speed upper limit and an engine power target is equal to an engine power temporary target, the drive control apparatus calculates an electrical power target that is equal to a charge/discharge power target (a discharge power target, in this case). On the other hand, when, in order for an engine speed temporary target not to exceed an engine speed upper limit, the engine power temporary target is limited by and thus equal to the engine speed upper limit, and an engine power target is less than an engine power temporary target, the drive control apparatus calculates an electrical power target that is equal to a value greater than a charge/discharge power target (a discharge power target, in this case).

The drive control apparatus restricts the electrical power target by the electrical power upper and lower limits which are finally selected after referring to the lookup tables 49$a$, 49$b$ and 49$c$ versus battery temperature, battery voltage and battery SOC (step S16, step S17).

The drive control apparatus controls the air intake condition by air quantity adjustment means 10, the fuel supply condition by fuel supply means 11 and the ignition condition by ignition means 12 so that the calculated engine operating point calculated in the above-mentioned way, especially, the engine torque target, may be realized.

On the other hand, the drive control apparatus calculates torque commands to control the first and second motor generators 4 and 5 based on the before-mentioned calculated engine operating point target, electrical power target and so forth.

That is, the drive control apparatus calculates a drive shaft rotational speed Nout of the planetary gear arrangements, and rotational speeds Nmg1t and Nmg2t for first and second motor generators 4 and 5 based on the calculated drive shaft driving rotational speed Nout (step S21). Then, the drive control apparatus calculates a torque base Tmg1i for first motor generator 4 based on electrical power target Pbatt, first and second motor generator speeds Nmg1t and Nmg2t, and engine torque target Tengt (step S22). On the other hand, the drive control apparatus calculates a torque base Tmg2i for second motor generator 5 based on the calculated torque base Tmg1i for first motor generator 4 and engine torque target Tengt (step S23). Moreover, the drive control apparatus calculates feedback torque corrections Tmg1fb and Tmg2fb for first and second motor generators 4 and 5 based on the engine speed and the engine speed target (step S24).

This enables the drive control apparatus to calculate the torque commands for first and second motor generators 4 and 5 based on the calculated torque bases Tmg1i and Tmg2i for first and second motor generators 4 and 5, and the feedback torque corrections Tmg1fb and Tmg2fb for first and second motor generators 4 and 5 (step S25).

The drive control apparatus provides those torque commands Tmg1i and Tmg2i for first and second motor generators 4 and 5 which have been calculated as mentioned above to first and second inverters 19 and 20, respectively. First and second inverters 19 and 20 regulate first and second motor generators 4 and 5 based on such torque commands Tmg1i and Tmg2i for them, respectively. This enables first and second motor generators 4 and 5 to operate in power running mode or in regenerating mode. As a result, the drive control apparatus may realize the battery charging/discharge target for the battery 21 while realizing the drive torque target.

Effect of the Present Embodiment

In the present embodiment, an engine speed final target is calculated so that an engine speed temporary target on that engine operating point temporary target which has been calculated from an initially calculated engine power temporary target fails to exceed an upper limit; based on the engine speed final target, an engine operating point target is recalculated; based on the recalculated engine operating point target, an engine power final target is calculated; based on the engine power final target which is restricted within a range defined by electrical power upper and lower limits calculated in response to the battery state, an electrical power target is calculated; and based on the calculated engine operating point target and electrical power target, the motor generators 4 and 5 are regulated, that is, the motor generators 4 and 5 are regulated to operate in power running mode or regenerating mode, together with regulation of the torque of the engine 2 based on the engine operating point target (the engine torque final target, in particular).

This prevents, in the present embodiment, the engine speed from becoming too high by calculating an engine speed target so that it may not exceed the upper limit, and enables realization of desired operation in power running mode or regenerating mode by the motor generators 4 an 5 because an electrical power target is calculated based on the engine speed target calculated not to exceed the upper limit. Therefore, the drive torque requested by the vehicle driver may be satisfied by a power assist created using the electrical power of the battery 21 while the SOC of the battery 21 is kept within a predetermined range and the engine speed is prevented from increasing too high.

In the present embodiment, there is provided protection from overvoltage, overdischarge and overcharge in response to the state of the battery 21 because the electrical power target is calculated as restricted within the range between the electrical upper and lower limits which have been calculated in response to the state of the battery 21.

On the other hand, in the present embodiment, an engine operating point target is calculated based on an engine speed first target that is so calculated as not to exceed an upper limit, and an electrical power target, as determined in consideration of a drive power target, is calculated based on the calculated engine operating point target. That is, according to the present embodiment, an appropriate engine operating point is determined while realizing a drive power target and an electrical power target.

For the above reason, in the present embodiment, taking the engine operating point into consideration, both the drive power which is aimed at and the state of charge/discharge which is aimed at (SOC kept within a predetermined range) are ensured.

In the present embodiment, an engine power target is calculated not to exceed the power upper limit which has been set for an engine power temporary target.

This ensures, in the present embodiment, a power-assist range using electrical power from the battery 21, regulating the engine so that its operating point may be adjusted to an optimal operating point and keeping the SOC of the battery 21 within a predetermined range. Therefore, the present embodiment enables propelling the vehicle using electrical power from the battery 21 by utilizing the power-assist range in response to the vehicle driver's request. Moreover, the two or more motor generators 4 and 5 may be regulated during charge/discharge of the battery 21.

Moreover, in this embodiment, among electrical power upper limits, one for battery charging and the other for battery discharging, obtained versus battery temperature by referring to the lookup table accessible by battery temperature 49a; electrical power upper limits, one for battery charging and the other for battery discharging, obtained versus battery voltage by referring to the lookup table accessible by battery voltage 49b; and electrical power upper limits, one for battery charging and the other for battery discharging, obtained versus SOC of battery 21 by referring to the lookup table accessible by battery SOC 49c, the electrical power upper and lower limit calculation function 51 evaluates each of the obtained upper limits according to how much an electrical power target is restricted to finally determine that one of the obtained upper limits for battery charging which has the greatest amount when the electrical power target is restricted and that one of the obtained upper limit for battery discharging which has the greatest amount when the electrical power target is restricted.

This allows calculation of the optimal electrical power upper limits, one for battery charging and the other for battery discharging, that is, the optimal electrical power upper and lower limits, in consideration of battery temperature, battery voltage and SOC.

On the other hand, in the present embodiment, an engine speed upper limit is calculated based on the vehicle speed and the rotational speed upper limit for first motor generator 4.

Therefore, the present embodiment makes it possible to calculate the appropriate engine speed upper limit agreeable with the property of the hybrid electric vehicle according to the present embodiment which limits the engine speed upper limit of the engine 2 with the rotational speed upper limit of first motor generator 4 and allows it to vary in response to the vehicle speed.

In the present embodiment, a feedback correction is provided for each of torque commands to motor generators 4 and 5 in order to let an actual engine speed approach an engine speed target determined from an engine operating target. Thus, in the present embodiment, fine correction of the torque commands to motor generators 4 and 5 may be made by providing the feedback corrections in this manner, making it possible to let the engine speed quickly approach the engine speed target. Thus, in this embodiment, the engine operating point may quickly agree with the operating point target, making it possible to quickly realize the appropriate operating state.

Preferably, in the present embodiment, it is desirable to apply a drive control apparatus, for a hybrid electric vehicle, which controls drive power of the vehicle using outputs of an engine and a plurality of motor generators, to a drive control apparatus, for a hybrid electric vehicle, which includes: an accelerator pedal position detection function for detecting an accelerator pedal position; a vehicle speed detection function for detecting vehicle speed; a battery state-of-charge detection function for detecting state-of-charge of a battery; a drive power target setup function for setting up a drive power target based on the accelerator pedal position detected by the accelerator pedal position detecting function and the vehicle speed detected by the vehicle speed detection function; a charge/discharge power target setup function for setting up a charge/discharge power target based on at least the state-of-charge of the battery detected by the battery state-of-charge detection function; and a motor torque command determination function for setting up torque commands for the plurality of motor generators.

Moreover, in the present embodiment, it is also possible to use at least one of the lookup table accessible by battery temperature 49a, the lookup table accessible by battery voltage 49b and the lookup table accessible by battery SOC 49c to calculate the electrical power upper limit and lower limit. Preferably, at least the lookup table accessible by battery temperature 49a and the lookup table accessible by battery voltage 49b are used to calculate the electrical power upper limit and lower limit. In such a case, in the present embodiment, the optimal electrical power upper limit and lower limit may be calculated in consideration of battery temperature and voltage.

With regard to the preceding description of the embodiment, it should not be understood that the scope of this invention is limited to the illustrated and described exemplary embodiments, and all the embodiments which brings equal effects which the present invention aims at are also involved. Furthermore, the scope of the present invention should not be limited to the combination of features of the invention defined in claim 1, but may be defined by any one of desired combinations of the specific features selected from all of the disclosed features.

DESCRIPTION OF NOTATIONS

1 Drive control apparatus for a hybrid electric vehicle; 40 Engine control; 41 Drive target calculation function; 42 Drive power target calculation function; 43 Charge/discharge power target calculation function; 44 Engine power temporary target calculation function; 45 Power upper limit calculation function; Engine operating point temporary target calculation function; 46a, 48a Maps for retrieval of engine operating point target; 47 Engine speed upper limit calculation function; 48 Engine operating point target calculation function; 49 Engine power target calculation function; 50 Electrical power target calculation function; 51 Electrical power upper and lower limit calculation function and 60 Motor generator control.

What is claimed is:

1. A drive control apparatus for providing a drive control to a hybrid electric vehicle by controlling an engine and motor generators, which are operable to give a charge of electrical power to a battery and receive a supply of electrical power from said battery, to power the vehicle with driving force derived from said engine and said motor generators, the drive control apparatus comprising:

a drive power target calculation function for calculating a drive power target based on an accelerator pedal position and the vehicle speed;

a charge/discharge target calculation function for calculating a charge/discharge electrical power target to/from said battery based on a state of charge/discharge of said battery;

an engine power first target calculation function for calculating an engine power first target based on the drive power target, which is calculated by said drive power target calculation function, and the charge/discharge electrical power target, which is calculated by said charge/discharge electrical power target calculation function;

an engine operating point first target calculation function for calculating an engine speed first target and an engine torque first target, both of which correspond to the engine power first target calculated by said engine power first target calculation function, based on information of the engine operating point identified by the relation between engine speed and engine torque;

an engine speed first target upper limit calculation function for calculating an upper limit of said engine speed first target based on the vehicle speed;

an engine speed second target calculation function for calculating an engine speed second target indicative of the engine speed first target which is calculated by said engine operating point calculation function so as not to exceed that upper limit of the engine speed first target which is calculated by said engine speed first target upper limit calculation function;

an engine torque second target calculation function for calculating an engine torque second target, which corresponds to said engine speed second target calculated by said engine speed second target calculation function, based on said information of the engine operating point;

an engine power second target calculation function for calculating an engine power second target based on the engine speed second target which is calculated by said engine speed second target calculation function and the engine torque second target which is calculated by said engine torque second target calculation function;

an electrical power upper and lower limit calculation function for calculating an electrical power upper limit for battery charging and an electrical power upper limit for battery discharging based on the state of said battery;

an electrical power target calculation function for calculating an electrical power target indicative of the amount of electrical power to be generated by driving said motor generators to charge said battery or to be provided by said battery to said motor generators to drive said motor generators, based on a difference between the drive power target which is calculated by said drive power target calculation function and the engine power second target which is calculated by said engine power second target calculation function, so that said calculated electrical power target may not exceed the electrical power upper limit for battery charging and the electrical power upper limit for battery discharging which are calculated by said electrical power upper limit calculation function;

an engine control configured to control torque of said engine based on the engine torque second target which is calculated by said engine torque second target calculation function; and a motor generator control configured to control said motor generators based on the engine speed second target which is calculated by said engine speed second target calculation function, the engine torque second target which is calculated by said engine torque second target calculation function, and the electrical power target which is calculated by said electrical target calculation function.

2. The drive control apparatus according to claim 1, further comprising:

a lookup table accessible by battery temperature for relating battery temperature to corresponding values of an electrical power upper limit for battery charging and also to corresponding values of an electrical power upper limit for battery discharging; and a lookup table accessible by battery voltage for relating battery voltage to corresponding values of an electrical power upper limit for battery charging and also to corresponding values of an electrical power upper limit for battery discharging, wherein among the electrical power upper limits, one for battery charging and the other for battery discharging, obtained versus battery temperature by referring to the lookup table accessible by battery temperature and the electrical power upper limits, one for battery charging and the other for battery discharging, obtained versus battery voltage by referring to the lookup table accessible by battery voltage, said electrical power upper and lower limit calculation function evaluates each of the obtained upper limits according to how much the electrical power target is restricted to finally determine that one of the obtained upper limits for battery charging which has the greatest amount when the electrical power target is restricted and that one of the obtained upper limits for battery discharging which has the greatest amount when the electrical power target is restricted.

3. The drive control apparatus according to claim 2, further comprising:

a lookup table accessible by battery state of charge (SOC) for relating battery SOC to corresponding values of an electrical power upper limit for battery charging and also to corresponding values of an electrical power upper limit for battery discharging, wherein among the electrical power upper limits, one for battery charging and the other for battery discharging, obtained versus battery temperature by referring to the lookup table accessible by battery temperature; the electrical power upper limits, one for battery charging and the other for battery discharging, obtained versus battery voltage by referring to the lookup table accessible by battery voltage; and the electrical power upper limits, one for battery charging and the other for battery discharging, obtained versus the state of charge of said battery by referring to the lookup table accessible by battery SOC, said electrical power upper and lower limit calculation function evaluates each of the obtained upper limits according to how much the electrical power target is restricted to finally determine that one of the obtained upper limits for battery charging which has the greatest amount when the electrical power target is restricted and that one of the obtained upper limits for battery discharging which has the greatest amount when the electrical power target is restricted.

4. The drive control apparatus according to claim 1, comprising a power split and composition system having four axes with each of rotary elements of two planetary gear arrangements connected;

wherein two motor generators are connected to said battery;

wherein, in a manner that one of said motor generators, said engine, a drive shaft connected to a traction wheel, and the other of said motor generators are located on a collinear diagram, the four axes of said power split and composition system are connected to said one motor generator, said engine, said drive shaft and said the other motor generator, respectively;

wherein an upper limit of said engine speed is restricted by an upper limit of rotational speed of said one motor generator and undergoes a change depending on the vehicle speed; and wherein said engine speed first target upper limit calculation function calculates the upper limit of said engine speed first target based on said vehicle speed and an upper limit of rotational speed of said one motor generator.

5. A hybrid electric vehicle including a drive control apparatus according to claim 1.

6. A drive control method for providing a drive control to a hybrid electric vehicle by controlling an engine and motor generators, which are operable to give a charge of electrical power to a battery and receive a supply of electrical power from said battery, to power the vehicle with driving force derived from said engine and said motor generators, the drive control method comprising the steps of:

calculating a drive power target based on an accelerator pedal position and the vehicle speed;

calculating a charge/discharge electrical power target to/from said battery based on a state-of-charge/discharge of said battery;

calculating an engine power first target based on said drive power target and said charge/discharge electrical power target;

calculating an engine speed first target and an engine torque first target, both of which correspond to said engine power first target, based on information of the engine operating point identified by the relation between engine speed and engine torque;

calculating an upper limit of said engine speed first target based on the vehicle speed;

calculating an engine speed second target indicative of the engine speed first target so as not to exceed said upper limit of the engine speed first target;

calculating an engine torque second target, which corresponds to said engine speed second target, based on said information of engine operating point;

calculating an engine power second target based on said engine speed second target and said engine torque second target;

calculating an electrical power upper limit for battery charging and an electrical power upper limit for battery discharging based on the state of said battery;

calculating an electrical power target indicative of the amount of electrical power to be generated by driving said motor generators to charge said battery or to be provided by said battery to said motor generators to drive said motor generators, based on a difference between said drive power target and said engine power second target, so that said calculated electrical power target may not exceed the electrical power upper limit for battery charging and the electrical power upper limit for battery discharging; and controlling said motor generators based on said engine speed second target, said engine torque second target, and said electrical power target together with controlling torque of said engine based on said engine torque second target.

\* \* \* \* \*